(12) United States Patent
Wei et al.

(10) Patent No.: US 11,419,805 B2
(45) Date of Patent: Aug. 23, 2022

(54) AEROSOL FOAM SKIN CLEANSER

(71) Applicant: The Procter & Gamble Company, Cincinnati, OH (US)

(72) Inventors: Karl Shiqing Wei, Mason, OH (US); Jean Jianqun Zhao, Cincinnati, OH (US); Somil Manjul Shah, Jersey City, NJ (US); Wei Ji, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/108,560

(22) Filed: Dec. 1, 2020

(65) Prior Publication Data

US 2021/0077372 A1    Mar. 18, 2021

Related U.S. Application Data

(63) Continuation of application No. 16/165,086, filed on Oct. 19, 2018, now abandoned.

(60) Provisional application No. 62/574,803, filed on Oct. 20, 2017.

(51) Int. Cl.
| | |
|---|---|
| *A61K 8/00* | (2006.01) |
| *A61K 8/46* | (2006.01) |
| *A61K 8/37* | (2006.01) |
| *A61K 8/87* | (2006.01) |
| *A61K 8/04* | (2006.01) |
| *A61K 8/31* | (2006.01) |
| *A61K 8/34* | (2006.01) |
| *A61K 8/92* | (2006.01) |
| *A61Q 19/10* | (2006.01) |
| *B65D 83/62* | (2006.01) |

(52) U.S. Cl.
CPC .............. *A61K 8/463* (2013.01); *A61K 8/046* (2013.01); *A61K 8/31* (2013.01); *A61K 8/342* (2013.01); *A61K 8/375* (2013.01); *A61K 8/87* (2013.01); *A61K 8/922* (2013.01); *A61Q 19/10* (2013.01); *A61K 2800/30* (2013.01); *A61K 2800/87* (2013.01); *B65D 83/62* (2013.01)

(58) Field of Classification Search
CPC .......... A61K 8/463; A61K 8/046; A61K 8/31
See application file for complete search history.

(56) References Cited

U.S. PATENT DOCUMENTS

| | | |
|---|---|---|
| 2,020,454 A | 11/1935 | Spaulding |
| 2,438,091 A | 3/1948 | Lynch |
| 2,528,378 A | 10/1950 | McCabe, Jr. |
| 2,658,072 A | 11/1953 | Kosmin |
| 2,798,053 A | 7/1957 | Brown |
| 2,986,271 A | 5/1961 | Forrer |

(Continued)

FOREIGN PATENT DOCUMENTS

| | | |
|---|---|---|
| CN | 1145026 A | 3/1997 |
| CN | 1153468 A | 7/1997 |

(Continued)

OTHER PUBLICATIONS

U.S. Appl. No. 16/943,888, filed Jul. 30, 2020, Wei et al.

(Continued)

*Primary Examiner* — Necholus Ogden, Jr.
(74) *Attorney, Agent, or Firm* — John G. Powell

(57) ABSTRACT

A packaged aerosol foaming skin cleanser can include a multiphase skin cleansing composition, a low pressure foaming agent, and a package.

14 Claims, 2 Drawing Sheets

(56) References Cited

U.S. PATENT DOCUMENTS

| | | |
|---|---|---|
| 3,455,440 A | 7/1969 | West |
| 3,479,429 A | 11/1969 | Morshauser |
| 3,533,955 A | 10/1970 | Pader |
| 3,542,256 A | 11/1970 | Waterman |
| D220,248 S | 3/1971 | Blumenthal |
| 3,618,757 A | 11/1971 | Funkhouser |
| 3,800,898 A | 4/1974 | Griffin |
| 3,850,365 A | 11/1974 | Dietrich |
| 3,852,475 A | 12/1974 | Tarangul |
| 3,899,076 A | 8/1975 | Florian |
| 3,915,921 A | 10/1975 | Schlatzer, Jr. |
| 3,926,861 A | 12/1975 | Gerecht |
| 3,929,678 A | 12/1975 | Laughlin et al. |
| 3,937,811 A | 2/1976 | Papantoniou |
| 3,940,351 A | 2/1976 | Schlatzer, Jr. |
| 3,951,679 A | 4/1976 | Bernhard |
| 3,980,767 A | 9/1976 | Chown |
| 4,062,817 A | 12/1977 | Westerman |
| 4,159,028 A | 6/1979 | Barker |
| 4,263,363 A | 4/1981 | Buck |
| 4,335,103 A | 6/1982 | Barker |
| 4,379,753 A | 4/1983 | Bolich, Jr. |
| 4,384,096 A | 5/1983 | Sonnabend |
| 4,421,902 A | 12/1983 | Chang |
| 4,425,322 A | 1/1984 | Harvey |
| 4,429,097 A | 1/1984 | Chang |
| 4,514,552 A | 4/1985 | Shay |
| 4,518,578 A | 5/1985 | Hayes |
| 4,600,761 A | 7/1986 | Ruffner |
| 4,616,074 A | 10/1986 | Ruffner |
| D292,879 S | 11/1987 | Smith |
| 4,743,698 A | 5/1988 | Ruffner |
| 4,772,427 A | 9/1988 | Dawson |
| 4,814,160 A | 3/1989 | Carter |
| RE3,300 E | 8/1989 | Ruffner et al. |
| 4,879,114 A | 11/1989 | Catsimpoolas |
| RE3,315 E | 1/1990 | Shay et al. |
| 4,966,205 A | 10/1990 | Tanaka |
| 4,980,155 A | 12/1990 | Shah |
| 5,002,680 A | 3/1991 | Schmidt |
| 5,011,681 A | 4/1991 | Ciotti |
| 5,059,414 A | 10/1991 | Dallal |
| 5,104,646 A | 4/1992 | Bolich, Jr. |
| 5,106,609 A | 4/1992 | Bolich, Jr. |
| 5,135,748 A | 8/1992 | Ziegler |
| 5,147,576 A | 9/1992 | Montague |
| 5,223,315 A | 6/1993 | Katsura |
| 5,228,912 A | 7/1993 | Herget |
| 5,292,843 A | 3/1994 | Jenkins |
| 5,294,692 A | 3/1994 | Barron |
| 5,304,334 A | 4/1994 | Lahanas |
| 5,342,883 A | 8/1994 | Jenkins |
| 5,364,617 A | 11/1994 | Bush |
| 5,393,450 A | 2/1995 | Shana |
| 5,412,142 A | 5/1995 | Wilkerson, III |
| 5,455,035 A | 10/1995 | Guerrero |
| 5,462,963 A | 10/1995 | Bush |
| 5,487,168 A | 1/1996 | Geiner |
| 5,487,884 A | 1/1996 | Bissett |
| 5,523,619 A | 6/1996 | Mcallister |
| 5,540,853 A | 7/1996 | Trinh |
| 5,556,628 A | 9/1996 | Derian |
| 5,578,299 A | 11/1996 | Starch |
| 5,612,307 A | 3/1997 | Chambers |
| 5,632,420 A | 5/1997 | Lohrman |
| 5,635,171 A | 6/1997 | Nadaud |
| 5,652,228 A | 7/1997 | Bissett |
| 5,661,189 A | 8/1997 | Grieveson |
| 5,681,852 A | 10/1997 | Bissett |
| 5,687,779 A | 11/1997 | Andersson |
| 5,716,920 A | 2/1998 | Glenn, Jr. |
| 5,770,760 A | 6/1998 | Robinson |
| 5,816,451 A | 10/1998 | Renault |
| 5,851,978 A | 12/1998 | Shana |
| 5,873,494 A | 2/1999 | Dallas, Jr. |
| 5,874,495 A | 2/1999 | Robinson |
| 5,914,117 A | 6/1999 | Lavaud |
| 5,916,575 A | 6/1999 | Mcatee |
| 5,925,603 A | 7/1999 | D'Angelo |
| 5,929,019 A | 7/1999 | Puvvada |
| 5,947,335 A | 9/1999 | Milio |
| 5,952,286 A | 9/1999 | Puvvada |
| 5,954,213 A | 9/1999 | Gerhart |
| 5,965,500 A | 10/1999 | Puvvada |
| 5,965,501 A | 10/1999 | Rattinger |
| 5,965,502 A | 10/1999 | Balzer |
| 5,972,361 A | 10/1999 | Fowler |
| 6,051,386 A | 4/2000 | Lerner |
| 6,068,834 A | 5/2000 | Kvalnes |
| D426,158 S | 6/2000 | Underwood |
| 6,150,312 A | 11/2000 | Puvvada et al. |
| 6,150,313 A | 11/2000 | Harmalker et al. |
| 6,165,395 A | 12/2000 | Kieras |
| 6,174,845 B1 | 1/2001 | Rattinger |
| 6,176,391 B1 | 1/2001 | Rehkemper |
| 6,190,648 B1 | 2/2001 | Kouzu |
| 6,194,364 B1 | 2/2001 | Glenn, Jr. |
| D438,460 S | 3/2001 | Hammond |
| D439,165 S | 3/2001 | Erckelbout |
| 6,213,166 B1 | 4/2001 | Thibiant |
| 6,217,888 B1 | 4/2001 | Oblong |
| D441,645 S | 5/2001 | Longhurst |
| 6,232,496 B1 | 5/2001 | Carr |
| 6,245,323 B1 | 6/2001 | Christie |
| 6,245,344 B1 | 6/2001 | Thibiant |
| 6,268,322 B1 | 7/2001 | St. Lewis et al. |
| D446,121 S | 8/2001 | Maddy |
| 6,270,446 B1 | 8/2001 | Abelbeck |
| D448,678 S | 10/2001 | Bakic |
| 6,306,806 B1 | 10/2001 | St. Lewis et al. |
| 6,335,312 B1 | 1/2002 | Coffindaffer |
| 6,338,855 B1 | 1/2002 | Albacarys |
| 6,340,723 B1 | 1/2002 | Nitta |
| D455,655 S | 4/2002 | Bunce |
| 6,367,519 B2 | 4/2002 | Thibiant |
| 6,383,999 B1 | 5/2002 | Coyle |
| 6,385,992 B1 | 5/2002 | Flore, Jr. |
| 6,394,323 B2 | 5/2002 | Mcclean |
| 6,395,691 B1 | 5/2002 | Tsaur |
| 6,407,044 B2 | 6/2002 | Dixon |
| 6,413,192 B2 | 7/2002 | Abelbeck |
| 6,419,783 B1 | 7/2002 | Rainey |
| 6,426,326 B1 | 7/2002 | Mitra |
| 6,429,177 B1 | 8/2002 | Williams |
| 6,433,061 B1 | 8/2002 | Marchant |
| D467,807 S | 12/2002 | Bakic |
| 6,495,498 B2 | 12/2002 | Niemiec |
| 6,506,391 B1 | 1/2003 | Biatry |
| 6,516,838 B2 | 2/2003 | Thibiant |
| 6,517,939 B1 | 2/2003 | Moini |
| 6,521,216 B1 | 2/2003 | Glandorf |
| 6,523,457 B1 | 2/2003 | Ancona |
| 6,534,456 B2 | 3/2003 | Hayward |
| 6,534,457 B2 | 3/2003 | Mitra |
| 6,534,458 B1 | 3/2003 | Kakizawa |
| 6,537,527 B1 | 3/2003 | Kvalnes |
| 6,547,063 B1 | 4/2003 | Zaveri |
| 6,555,509 B2 | 4/2003 | Abbas et al. |
| 6,564,978 B1 | 5/2003 | Safian |
| 6,574,985 B2 | 6/2003 | Fiore, Jr. |
| 6,589,509 B2 | 7/2003 | Keller |
| 6,635,702 B1 | 10/2003 | Schmucker-Castner |
| 6,645,511 B2 | 11/2003 | Aronson |
| 6,652,134 B2 | 11/2003 | Lloyd |
| 6,660,251 B1 | 12/2003 | Buenger et al. |
| 6,663,855 B2 | 12/2003 | Frechet |
| 6,673,371 B2 | 1/2004 | Brown |
| 6,673,755 B2 | 1/2004 | Wei |
| D486,398 S | 2/2004 | Lovell |
| 6,691,394 B1 | 2/2004 | Mcclean |
| 6,695,510 B1 | 2/2004 | Look |
| 6,716,440 B2 | 4/2004 | Aronson |
| 6,723,688 B1 | 4/2004 | Malik |
| 6,727,209 B2 | 4/2004 | Pereira |

(56) References Cited

U.S. PATENT DOCUMENTS

| | | |
|---|---|---|
| 6,759,376 B2 | 7/2004 | Zhang |
| 6,780,826 B2 | 8/2004 | Zhang |
| 6,849,584 B2 | 2/2005 | Geary |
| D502,400 S | 3/2005 | Cinquino |
| D505,079 S | 5/2005 | Mulder |
| 6,897,253 B2 | 5/2005 | Schmucker-castner |
| 6,919,303 B2 | 7/2005 | Pham |
| 6,924,256 B2 | 8/2005 | Massaro |
| D525,872 S | 8/2006 | Haubert |
| D525,873 S | 8/2006 | Haubert |
| 7,084,104 B2 | 8/2006 | Martin et al. |
| 7,098,180 B2 | 8/2006 | Ganopolsky et al. |
| D527,637 S | 9/2006 | Bakic |
| D528,005 S | 9/2006 | Bakic |
| D529,388 S | 10/2006 | Bakic |
| D529,810 S | 10/2006 | Davies |
| 7,119,059 B2 | 10/2006 | Librizzi et al. |
| D533,784 S | 12/2006 | Bakic |
| 7,143,893 B2 | 12/2006 | Kelly |
| 7,144,542 B2 | 12/2006 | Holzer |
| 7,157,414 B2 | 1/2007 | Librizzi et al. |
| 7,229,486 B2 | 6/2007 | Wiersema |
| 7,229,778 B2 | 6/2007 | Hendrix |
| 7,268,104 B2 | 9/2007 | Krzysik |
| 7,273,837 B2 | 9/2007 | Boutique |
| 7,288,616 B2 | 10/2007 | Tamareselvy |
| 7,354,926 B2 | 4/2008 | Lintner |
| 7,488,707 B2 | 2/2009 | Frantz |
| 7,511,003 B2 | 3/2009 | Focht et al. |
| 7,524,807 B2 | 4/2009 | Clapp |
| 7,527,077 B2 | 5/2009 | Mccall |
| 7,531,497 B2 | 5/2009 | Midha et al. |
| 7,537,819 B2 | 5/2009 | Hendricks |
| D601,425 S | 10/2009 | Miller |
| D601,648 S | 10/2009 | Cornelio, Jr. |
| D608,648 S | 1/2010 | Rhodes |
| 7,649,047 B2 | 1/2010 | Tamareselvy |
| 7,666,825 B2 | 2/2010 | Wagner et al. |
| 7,737,104 B2 | 6/2010 | Hilliard, Jr. |
| 7,749,951 B2 | 7/2010 | Hilliard, Jr. |
| 7,754,666 B2 | 7/2010 | Walters |
| 7,754,667 B2 | 7/2010 | Walters |
| 7,761,242 B2 | 7/2010 | Honkonen |
| 7,763,419 B2 | 7/2010 | Hendrix et al. |
| 7,767,389 B2 | 8/2010 | Hendrix et al. |
| 7,771,924 B2 | 8/2010 | Hendrix et al. |
| 7,771,925 B2 | 8/2010 | Hendrix et al. |
| 7,776,346 B2 | 8/2010 | Oconnor |
| 7,803,403 B2 | 9/2010 | Librizzi |
| 7,820,609 B2 | 10/2010 | Soffin |
| 7,906,475 B2 | 3/2011 | Walters |
| 7,954,392 B2 | 6/2011 | Belcher |
| D641,633 S | 7/2011 | Carnduff |
| D644,106 S | 8/2011 | Almstead, Jr. |
| 8,025,902 B2 | 9/2011 | Librizzi |
| D646,170 S | 10/2011 | Carnduff |
| 8,029,772 B2 | 10/2011 | Frantz |
| 8,067,517 B2 | 11/2011 | Yoshinaka |
| 8,093,192 B2 | 1/2012 | Liu |
| 8,105,996 B2 | 1/2012 | Wei |
| 8,124,064 B2 | 2/2012 | Wei |
| 8,124,573 B2 | 2/2012 | Focht |
| 8,147,853 B2 | 4/2012 | Taylor |
| 8,158,566 B2 | 4/2012 | Wei |
| D660,181 S | 5/2012 | Nowacek |
| D660,704 S | 5/2012 | Simmons |
| D660,705 S | 5/2012 | Simmons |
| 8,283,852 B2 | 10/2012 | Lee |
| 8,309,667 B2 | 11/2012 | Yoshinaka |
| D674,282 S | 1/2013 | Baldridge et al. |
| D674,292 S | 1/2013 | Klich |
| 8,394,361 B1 | 3/2013 | Frantz |
| 8,417,474 B2 | 4/2013 | Datta |
| D683,226 S | 5/2013 | Baldridge |
| 8,518,991 B2 | 8/2013 | Gunn |
| 8,772,212 B2 | 7/2014 | Restrepo et al. |
| 8,785,397 B2 | 7/2014 | Bernard |
| 8,795,679 B2 | 8/2014 | Einarsson |
| 8,840,871 B2 | 9/2014 | Wei |
| 9,101,551 B2 | 8/2015 | Stella |
| 9,162,085 B2 | 10/2015 | Dihora et al. |
| 9,186,642 B2 | 11/2015 | Dihora |
| 9,216,143 B2 | 12/2015 | Restrepo et al. |
| 9,352,289 B2 | 5/2016 | Beijne et al. |
| 9,671,410 B2 | 6/2017 | Stella |
| 9,675,530 B2 | 6/2017 | Focht |
| 9,717,674 B1 | 8/2017 | Guskey |
| 9,750,674 B2 | 9/2017 | Wei |
| 9,808,408 B2 | 11/2017 | Stella |
| 9,931,282 B2 | 4/2018 | Restrepo et al. |
| 9,943,468 B2 | 4/2018 | Stevenson |
| 10,085,924 B2 | 10/2018 | Wei |
| 10,588,858 B2 | 3/2020 | Tamarkin |
| 10,966,916 B2 | 4/2021 | Wei |
| 2001/0006088 A1 | 7/2001 | Lyle |
| 2002/0042448 A1 | 4/2002 | Sorrentino |
| 2002/0122772 A1* | 9/2002 | Lukenbach ......... A61K 8/0295 |
| | | 424/44 |
| 2002/0182112 A1 | 12/2002 | Thorn |
| 2003/0003069 A1 | 1/2003 | Carson |
| 2003/0083210 A1 | 5/2003 | Goldberg |
| 2003/0147842 A1 | 8/2003 | Restle et al. |
| 2003/0161852 A1 | 8/2003 | Miller |
| 2003/0171230 A1 | 9/2003 | Shana'a et al. |
| 2003/0180246 A1 | 9/2003 | Frantz |
| 2003/0207988 A1 | 11/2003 | Tamareselvy |
| 2003/0232101 A1 | 12/2003 | Travis |
| 2004/0009138 A1 | 1/2004 | Kling |
| 2004/0028932 A1 | 2/2004 | Holzer |
| 2004/0057920 A1 | 3/2004 | Focht |
| 2004/0091445 A1 | 5/2004 | Dykstra |
| 2004/0092415 A1 | 5/2004 | Focht |
| 2004/0092425 A1 | 5/2004 | Boutique |
| 2004/0105827 A1 | 6/2004 | Grimm |
| 2004/0146475 A1 | 7/2004 | Peffly |
| 2004/0158940 A1 | 8/2004 | Wells |
| 2004/0180020 A1 | 9/2004 | Manelski |
| 2004/0219119 A1 | 11/2004 | Wei |
| 2004/0223929 A1 | 11/2004 | Clapp |
| 2004/0223939 A1 | 11/2004 | Clausen |
| 2004/0223991 A1 | 11/2004 | Wei |
| 2004/0223992 A1 | 11/2004 | Clapp |
| 2004/0232023 A1 | 11/2004 | Bansal |
| 2004/0235693 A1 | 11/2004 | Wei |
| 2004/0235702 A1 | 11/2004 | Hawkins |
| 2004/0248748 A1 | 12/2004 | Wei |
| 2004/0248749 A1 | 12/2004 | Mitra |
| 2005/0003975 A1 | 1/2005 | Browne |
| 2005/0019299 A1 | 1/2005 | LiBrizzi et al. |
| 2005/0020468 A1 | 1/2005 | Frantz et al. |
| 2005/0049172 A1 | 3/2005 | Lukenbach et al. |
| 2005/0063930 A1 | 3/2005 | Carlsson |
| 2005/0070452 A1 | 3/2005 | Librizzi |
| 2005/0075256 A1 | 4/2005 | Librizzi |
| 2005/0100570 A1 | 5/2005 | Wei |
| 2005/0129759 A1 | 6/2005 | Sojka |
| 2005/0139574 A1 | 6/2005 | Simone |
| 2005/0143269 A1 | 6/2005 | Wei |
| 2005/0191709 A1 | 9/2005 | Hendrix |
| 2005/0192187 A1 | 9/2005 | Wagner |
| 2005/0192188 A1 | 9/2005 | Wagner |
| 2005/0192189 A1 | 9/2005 | Wagner |
| 2005/0221334 A1 | 10/2005 | Benson |
| 2005/0238680 A1 | 10/2005 | Stella |
| 2005/0249758 A1 | 11/2005 | Di Puccio Pagano |
| 2005/0269372 A1 | 12/2005 | Smith |
| 2005/0276768 A1 | 12/2005 | Wei |
| 2005/0287088 A1 | 12/2005 | Guiramand |
| 2006/0002880 A1 | 1/2006 | Peffly |
| 2006/0008438 A1 | 1/2006 | Velarde |
| 2006/0039986 A1 | 2/2006 | Okamoto et al. |
| 2006/0040834 A1 | 2/2006 | Hilliard |
| 2006/0042184 A1 | 3/2006 | Perkins |
| 2006/0079417 A1 | 4/2006 | Wagner |

(56) References Cited

U.S. PATENT DOCUMENTS

| | | |
|---|---|---|
| 2006/0079419 A1 | 4/2006 | Wagner et al. |
| 2006/0079420 A1 | 4/2006 | Wagner |
| 2006/0079421 A1 | 4/2006 | Wagner et al. |
| 2006/0094628 A1 | 5/2006 | Wei |
| 2006/0094635 A1 | 5/2006 | Pereira |
| 2006/0182699 A1 | 8/2006 | Taylor |
| 2006/0189495 A1 | 8/2006 | LiBrizzi et al. |
| 2006/0193800 A1 | 8/2006 | Reinhardt et al. |
| 2006/0210505 A1 | 9/2006 | Clapp |
| 2006/0257348 A1 | 11/2006 | Walters |
| 2006/0269501 A1 | 11/2006 | Johnson |
| 2006/0276357 A1 | 12/2006 | Smith, III |
| 2006/0276768 A1 | 12/2006 | Miller |
| 2007/0141001 A1 | 6/2007 | Clapp |
| 2007/0155637 A1 | 7/2007 | Smith, III |
| 2007/0187274 A1 | 8/2007 | Dalea |
| 2007/0196344 A1 | 8/2007 | Osborne |
| 2007/0202488 A1 | 8/2007 | Hendrix |
| 2007/0202489 A1 | 8/2007 | Hendrix |
| 2007/0202490 A1 | 8/2007 | Hendrix |
| 2007/0202491 A1 | 8/2007 | Hendrix |
| 2007/0224154 A1 | 9/2007 | Brumbaugh |
| 2007/0224696 A1 | 9/2007 | Honkonen |
| 2007/0248562 A1 | 10/2007 | Berry |
| 2007/0259796 A1 | 11/2007 | Fevola et al. |
| 2007/0280976 A1 | 12/2007 | Taylor |
| 2007/0286832 A1 | 12/2007 | Clapp |
| 2008/0039353 A1 | 2/2008 | Focht |
| 2008/0045428 A1 | 2/2008 | Focht |
| 2008/0045429 A1 | 2/2008 | Focht |
| 2008/0095733 A1 | 4/2008 | Griffin et al. |
| 2008/0112913 A1 | 5/2008 | Librizzi |
| 2008/0196787 A1 | 8/2008 | Comstock |
| 2008/0233061 A1 | 9/2008 | Gates et al. |
| 2008/0242573 A1 | 10/2008 | Wei |
| 2009/0005449 A1 | 1/2009 | Gunn |
| 2009/0005460 A1 | 1/2009 | Gunn |
| 2009/0028809 A1 | 1/2009 | Cetti |
| 2009/0042765 A1 | 2/2009 | Gizaw |
| 2009/0107062 A1 | 4/2009 | Pedersen |
| 2009/0148392 A1 | 6/2009 | SenGupta |
| 2009/0162443 A1 | 6/2009 | Anthony |
| 2009/0209600 A1 | 8/2009 | Miner |
| 2009/0220443 A1 | 9/2009 | Braksmayer |
| 2009/0227751 A1 | 9/2009 | Yoshinaka |
| 2009/0311348 A1 | 12/2009 | Einarsson |
| 2009/0324521 A1 | 12/2009 | Cetti |
| 2010/0020937 A1 | 1/2010 | Hautmann |
| 2010/0022454 A1 | 1/2010 | Norskov-lauritsen |
| 2010/0022455 A1 | 1/2010 | Chilkoti |
| 2010/0022456 A1 | 1/2010 | Christensen |
| 2010/0022458 A1 | 1/2010 | Kopke |
| 2010/0028376 A1 | 2/2010 | Einarsson |
| 2010/0040074 A1 | 2/2010 | Dropps |
| 2010/0040075 A1 | 2/2010 | Kalhoff |
| 2010/0048706 A1 | 2/2010 | Subramanyam |
| 2010/0105102 A1 | 4/2010 | Hanes |
| 2010/0158830 A1 | 6/2010 | Wei |
| 2010/0184847 A1 | 7/2010 | Shin |
| 2010/0190675 A1 | 7/2010 | Cetti |
| 2010/0216707 A1 | 8/2010 | Bernard |
| 2010/0317677 A1 | 12/2010 | Hassel |
| 2010/0322878 A1 | 12/2010 | Stella |
| 2011/0033842 A1 | 2/2011 | Moon |
| 2011/0038830 A1 | 2/2011 | Bernard |
| 2011/0045037 A1 | 2/2011 | Tamarkin |
| 2011/0045039 A1 | 2/2011 | Sunkel |
| 2011/0064688 A1 | 3/2011 | Jordan |
| 2011/0071123 A1 | 3/2011 | Schwartz |
| 2011/0089196 A1 | 4/2011 | Cetti |
| 2011/0091439 A1 | 4/2011 | Bernard |
| 2011/0117225 A1 | 5/2011 | Wei et al. |
| 2011/0162668 A1 | 7/2011 | Coffindaffer |
| 2011/0165607 A1 | 7/2011 | Takeda |
| 2011/0245124 A1 | 10/2011 | Tsaur et al. |
| 2011/0245125 A1 | 10/2011 | Tsaur |
| 2011/0247954 A1 | 10/2011 | Wei |
| 2011/0250141 A1 | 10/2011 | Wei |
| 2011/0251872 A1 | 10/2011 | Wei |
| 2011/0253157 A1 | 10/2011 | Wei |
| 2011/0253158 A1 | 10/2011 | Wei |
| 2011/0257020 A1 | 10/2011 | Stella |
| 2011/0257030 A1 | 10/2011 | Stella et al. |
| 2011/0257071 A1 | 10/2011 | Miralles |
| 2011/0262025 A1 | 10/2011 | Jarrold |
| 2011/0262570 A1 | 10/2011 | Finlay |
| 2011/0268802 A1 | 11/2011 | Dihora et al. |
| 2011/0269657 A1 | 11/2011 | Dihora |
| 2011/0280822 A1 | 11/2011 | Griffin |
| 2011/0281256 A1 | 11/2011 | Davis |
| 2011/0281366 A1 | 11/2011 | Davis |
| 2011/0305653 A1 | 12/2011 | Jordan |
| 2012/0009285 A1 | 1/2012 | Wei et al. |
| 2012/0010303 A1 | 1/2012 | Mujkic |
| 2012/0035557 A1 | 2/2012 | Coffindaffer |
| 2012/0087882 A1 | 4/2012 | Fevola |
| 2012/0093753 A1 | 4/2012 | Fevola |
| 2012/0128964 A1 | 5/2012 | Hulse et al. |
| 2012/0184448 A1 | 7/2012 | Stella et al. |
| 2012/0197016 A1 | 8/2012 | Laughlin, II |
| 2012/0258074 A1 | 10/2012 | Mills |
| 2012/0258126 A1 | 10/2012 | Schoeller |
| 2012/0276175 A1 | 11/2012 | Dihora et al. |
| 2012/0276177 A1 | 11/2012 | Hilliard, Jr. |
| 2012/0276210 A1 | 11/2012 | Dihora |
| 2012/0282309 A1 | 11/2012 | Dihora |
| 2012/0283112 A1 | 11/2012 | Binder |
| 2012/0316095 A1* | 12/2012 | Wei ............ C11D 3/226 510/159 |
| 2013/0115610 A1 | 5/2013 | Lanzalaco |
| 2013/0115648 A1 | 5/2013 | Lanzalaco |
| 2013/0149273 A1 | 6/2013 | Wei et al. |
| 2013/0183360 A1 | 7/2013 | Lips et al. |
| 2013/0202667 A1 | 8/2013 | An et al. |
| 2013/0225468 A1 | 8/2013 | Corominas |
| 2013/0253057 A1 | 9/2013 | Wei et al. |
| 2013/0280174 A1 | 10/2013 | Lipic |
| 2013/0280192 A1 | 10/2013 | Carter et al. |
| 2013/0280193 A1 | 10/2013 | Carter |
| 2013/0280202 A1 | 10/2013 | Stella |
| 2013/0280356 A1 | 10/2013 | Stella |
| 2013/0281551 A1 | 10/2013 | Stella et al. |
| 2013/0344012 A1 | 12/2013 | Cohen |
| 2014/0023606 A1 | 1/2014 | Scheunemann |
| 2014/0057997 A1 | 2/2014 | Chevalier |
| 2014/0072533 A1 | 3/2014 | Lanzalaco |
| 2014/0131395 A1 | 5/2014 | Chang |
| 2014/0197309 A1 | 7/2014 | Davis |
| 2014/0219946 A1 | 8/2014 | Hloucha |
| 2014/0273055 A1 | 9/2014 | Kerr et al. |
| 2014/0335532 A1 | 11/2014 | Finlay et al. |
| 2014/0357714 A1 | 12/2014 | Braksmayer |
| 2015/0071977 A1 | 3/2015 | Dihora |
| 2015/0096582 A1 | 4/2015 | Stella |
| 2015/0098920 A1 | 4/2015 | Stella |
| 2016/0122806 A1 | 5/2016 | Amini |
| 2016/0128913 A1 | 5/2016 | Wei et al. |
| 2016/0128917 A1 | 5/2016 | Wei |
| 2016/0128927 A1 | 5/2016 | Wei et al. |
| 2016/0128930 A1 | 5/2016 | Stella |
| 2016/0129917 A1 | 5/2016 | Gariepy |
| 2016/0310375 A1 | 10/2016 | Torres Rivera |
| 2017/0000711 A1 | 1/2017 | Jansen |
| 2017/0049673 A1 | 2/2017 | Wei |
| 2017/0165155 A1 | 6/2017 | Glenn, Jr. |
| 2017/0165164 A1 | 6/2017 | Zhao et al. |
| 2017/0174413 A1 | 6/2017 | Callens et al. |
| 2017/0228514 A1 | 8/2017 | Apte |
| 2017/0333315 A1 | 11/2017 | Wei |
| 2018/0055894 A1 | 3/2018 | Kim |
| 2018/0110704 A1 | 4/2018 | Zhao |
| 2018/0185255 A1 | 7/2018 | Wei |
| 2018/0353394 A1 | 12/2018 | Skubsch |
| 2018/0360706 A1 | 12/2018 | Dihora |

(56) References Cited

U.S. PATENT DOCUMENTS

| | | |
|---|---|---|
| 2019/0117537 A1 | 4/2019 | Wei |
| 2019/0117546 A1 | 4/2019 | Wei |
| 2019/0142714 A1 | 5/2019 | Dihora |
| 2019/0178774 A1 | 6/2019 | Wei |
| 2020/0040373 A1 | 2/2020 | Wei |
| 2020/0146967 A1 | 5/2020 | Wei |
| 2020/0172876 A1 | 6/2020 | Wei et al. |
| 2020/0360251 A1 | 11/2020 | Wei |

FOREIGN PATENT DOCUMENTS

| | | |
|---|---|---|
| CN | 1181006 A | 5/1998 |
| CN | 1248910 A | 3/2000 |
| CN | 1280488 A | 1/2001 |
| CN | 1298293 A | 6/2001 |
| CN | 103813780 A | 5/2014 |
| CN | 110804666 A | 2/2020 |
| DE | 20122018 U1 | 12/2003 |
| DE | 102008035172 A1 | 2/2010 |
| EP | 0078138 A2 | 5/1983 |
| EP | 0937495 A2 | 8/1999 |
| EP | 1005849 B1 | 9/2001 |
| EP | 1064918 B1 | 9/2002 |
| EP | 1243321 A1 | 9/2002 |
| EP | 0907345 | 5/2003 |
| EP | 1657159 B1 | 8/2007 |
| EP | 1383542 B1 | 4/2008 |
| EP | 2505180 A1 | 10/2012 |
| FR | 2233036 A1 | 1/1975 |
| FR | 2792728 A1 | 10/2000 |
| FR | 2908784 B1 | 5/2008 |
| FR | 2924613 B1 | 6/2009 |
| FR | 2924614 B1 | 6/2009 |
| FR | 2925314 B1 | 6/2009 |
| FR | 2924947 B1 | 3/2010 |
| GB | 2245585 A1 | 8/1992 |
| GB | 2431345 B | 5/2009 |
| JP | S61155311 A | 7/1986 |
| JP | H0395110 A | 4/1991 |
| JP | H04149112 A | 5/1992 |
| JP | 6262060 A | 9/1994 |
| JP | 8220550 A | 8/1996 |
| JP | 10216106 A | 8/1998 |
| JP | 2000229817 A | 8/2000 |
| JP | 2002128639 A | 5/2002 |
| JP | 2002138010 A | 5/2002 |
| JP | 2009084224 | 4/2009 |
| JP | 2009126791 A | 6/2009 |
| JP | 2010235567 A | 10/2010 |
| JP | 2011178667 A | 9/2011 |
| JP | 2016183134 A | 10/2016 |
| KR | 1020110068049 A | 6/2011 |
| KR | 1020120009774 A | 2/2012 |
| KR | 20170102857 A | 9/2017 |
| WO | 9212911 A1 | 8/1992 |
| WO | 9401084 A2 | 1/1994 |
| WO | 9410973 A1 | 5/1994 |
| WO | 9534280 A1 | 12/1995 |
| WO | 9602225 A1 | 2/1996 |
| WO | 9629979 A1 | 10/1996 |
| WO | 9717938 A1 | 5/1997 |
| WO | 9821299 A1 | 5/1998 |
| WO | 9827193 A1 | 6/1998 |
| WO | 9938491 A1 | 8/1999 |
| WO | WO-9938491 A1 * | 8/1999 ............ A61K 8/365 |
| WO | 9946319 A1 | 9/1999 |
| WO | 0030597 A1 | 6/2000 |
| WO | 0066612 A1 | 11/2000 |
| WO | 0067712 A1 | 11/2000 |
| WO | 0075240 A1 | 12/2000 |
| WO | 0101931 A2 | 1/2001 |
| WO | 0155497 A1 | 8/2001 |
| WO | 02100358 A1 | 12/2002 |
| WO | 03105796 A1 | 12/2003 |
| WO | 2006113117 A1 | 10/2006 |
| WO | 2007129330 A1 | 11/2007 |
| WO | 2007129331 A2 | 11/2007 |
| WO | 2008074624 A1 | 6/2008 |
| WO | 2009001260 A2 | 12/2008 |
| WO | WO2008148672 | 12/2008 |
| WO | 2009077995 A1 | 6/2009 |
| WO | 2009081368 A2 | 7/2009 |
| WO | 2009081374 A2 | 7/2009 |
| WO | 2010079468 A2 | 7/2010 |
| WO | 2011133538 A1 | 10/2011 |
| WO | 2012138710 A2 | 10/2012 |
| WO | 2015044315 A1 | 4/2015 |

OTHER PUBLICATIONS

C. Faller et al. "Predictive ability of reconstructed human epidermis equivalents for the assessment of skin irritation of cosmetics", Toxicology In Vitro., vol. 16, No. 5, Feb. 22, 2002, pp. 557-572.

Cheng Cheng Zhou et al. Self-Aggregation,Antibacterial Activity, and Mildness of Cyclodextrin/Cationic Trimeric Surfactant Complexes 11,ACS Applied Materials & Interfaces,vol. 8, No. 45,Nov. 7, 2016 (Nov. 7, 2016), pp. 30811-30823, XP055557529.

Chng et al. Whole metagenome profiling reveals skin microbiome-dependent susceptibility to atopic dermatitis flare. Nature Microbiology 2016, vol. 1, No. 16106, pp. 1-10 (Year: 2016).

Geert De Lathauwer, CD Proceeding 6th World Surfactant Congress CESIO, Berlin Germany, Jun. 2004 (paper# 154) (Year: 2004), 9 Pages.

Joachim W. Fluhrl et al. "Comparative study of five instruments measuring stratum corneum hydration (Comeometer CM 820 and CM 825, Skicon 200, Nova DPM 9003, DermaLab). Part 11. In vivo", Skin Research and Technology, Jan. 1, 1999, pp. 171-178.

Michael Starch et al., "New Cosmetic Ingredients Based on Metathesized Soybean Oil", ip.com Journal, ip.com Inc., West Henrietta, NY, US, Sep. 9, 2010 (Sep. 9, 2010), XP013140234. 11 Pages.

Product Data Sheet, N000557—Jun. 2009 (Year: 2009), 1 Page.

Rimpro India, Surfactant, 2011, 2 Pages.

Russel M. Walters et al., Cleansing Formulations That Respect Skin Barrier Integrity,A Dermatology Research and Practice,vol. 2012, Jan. 1, 2012 (Jan. 1, 2012),pp. 1-9, XP055557527.

Sam Osseiran et al. "Characterizing stratum corneum structure, barrier function, and chemical content of human skin with coherent Raman scattering imaging" Biomedical Optics Express, vol. 9. No. 12, Nov. 26, 2018, 19 Pages.

Scott Truong: "Design of a Handheld Skin Moisture Measuring Device for Application towards Eczema" Apr. 3, 2009, https://macsphere.mcmaster.ca/bitstream/11375/14416/1/fulltext.pdf, pp. 8, 9, 17 and 18.

Silva et al. Insights into the skin microbiome dynamics of leprosy patients during multi-drug therapy and in healthy individuals from Brazil. Scientific Reports Jun. 8, 2018, 8:8783, pp. 1-10 (Year: 2018).

Weber et al. Steroid-Free Over-the-Counter Eczema Skin Care Formulations Reduce Risk of Flare, Prolong Time to Flare, andu Reduce Eczema Symptoms in Pediatric Subjects With Atopic Dermatitis Journal of Drugs in Dermatology, 2015, vol. 14, Issue 5,pp. 478-485.

www.single-cell.cn/skin search results retrieved Oct. 5, 2019), 1 Page.

Zeng et al. High-Altitude Living Shapes the Skin Microbiome in Humans and Pigs. Frontiers in Microbiology 2017, vol. 8, article1929, pp. 1-10 (Year: 2017).

"Composition and Applications of Aloe Vera Leaf Gel", Josias H. Hamman, Published Aug. 8, 2008, Molecules 2008, 13, 1599-1616.

All final and non-final office actions for U.S. Appl. No. 12/054,853 (P&G Case 10780).

All final and non-final office actions for U.S. Appl. No. 12/814,307 (P&G Case 10780R).

All final and non-final office actions for U.S. Appl. No. 13/007,630 (P&G Case 11737).

All final and non-final office actions for U.S. Appl. No. 13/007,631.

All final and non-final office actions for U.S. Appl. No. 13/007,632.

All final and non-final office actions for U.S. Appl. No. 13/157,665.

(56) References Cited

OTHER PUBLICATIONS

All final and non-final office actions for U.S. Appl. No. 13/491,634.
All final and non-final office actions for U.S. Appl. No. 13/707,108.
All final and non-final office actions for U.S. Appl. No. 13/848,271.
All final and non-final office actions for U.S. Appl. No. 13/865,554.
All final and non-final office actions for U.S. Appl. No. 13/865,588.
All final and non-final office actions for U.S. Appl. No. 14/937,089.
All final and non-final office actions for U.S. Appl. No. 14/937,171.
All final and non-final office actions for U.S. Appl. No. 14/937,335.
All final and non-final office actions for U.S. Appl. No. 14/937,425.
All final and non-final office actions for U.S. Appl. No. 15/669,001.
All final and non-final office actions for U.S. Appl. No. 15/859,925.
All final and non-final office actions for U.S. Appl. No. 16/055,604.
All final and non-final office actions for U.S. Appl. No. 16/120,681.
All final and non-final office actions for U.S. Appl. No. 16/165,086.
All final and non-final office actions for U.S. Appl. No. 16/165,146.
All final and non-final office actions for U.S. Appl. No. 16/211,531.
All final and non-final office actions for U.S. Appl. No. 16/270,861.
All final and non-final office actions for U.S. Appl. No. 16/697,946.
All final and non-final office actions for U.S. Appl. No. 16/740,573.
All final and non-final office actions for U.S. Appl. No. 16/943,888.
All final and non-final office actions for U.S. Appl. No. 29/389,585.
All final and non-final office actions for U.S. Appl. No. 29/438,169.
Becker et al., Detection of Differentially Regulated Genes in Keratinocytes by cDNA Array Hybridization: Hsp27 and Other Novel Players in Response to Artificial Ultraviolet Radiation, Journal of Investigative Dermatology, vol. 116, No. 6, Jun. 2001, pp. 983-988.
Clariant "Mild Surfactants Clariant Mild Surfactants for Personal Care Applications" Jul. 23, 2015.
Cocamidopropyl betaine Product Specification, Edition 1, Jun. 2005.
Conti et al., Seasonal influences on stratum corneum ceramide 1 fatty acids and the influence of topical essential fatty acids, International Journal of Cosmetic Science 18, 1-12 (1996).
D.J. Burgess, Practical Analysis of Complex Coacervate Systems, Journal of Colloid and Interface Science, vol. 140, No. 1, Nov. 1990, pp. 227-238.
Erhirhie et al. Medicinal Values of *Citrullus lanatus* (Watermelon): Pharmacological Review. International Journal of Research in Pharmaceutical and Biomedical Sciences 2013, vol. 4, No. 4, pp. 1305-1312 (Year: 2013).
Ertel et al., Leg wash protocol to assess the skin moisturization potential of personal cleansing products, International Journal of Cosmetic Science, vol. 21, No. Dec. 6, 1999, pp. 383-397.
FDA CFR 21 201.57 (Apr. 1, 2008 edition).
Flores et al. Microbiome of Affected and Unaffected Skin of Patients with Atopic Dermatitis Before and After Emollient Treatment. Journal of Drugs in Dermatology 2014, vol. 13, issue 11, pp. 611-618 (Year: 2014).
Grando et al., Adrenergic and Cholinergic Control in the Biology of Epidermis: Physiological and Clinical Significance, Journal of Investigative Dermatology vol. 126, pp. 1948-1965 (2006).
Grice and Segre. The skin microbiome. Nature Reviews Microbiology 2011, vol. 9, pp. 244-253 (Year: 2011).
Household Products Database, Brand Information, "Olay Daily Renewal Moisturizing Body Wash, Calming, "[Online] URL: http://householdproducts.nlm.nih.gov/cgi-bin/household/brands?tbl=brands&id=16003084, accessed Feb. 8, 2006 (2 pages).
International Search Report and Written Opinion of the International Searching Authority PCT/US2010/040074 dated Jan. 21, 2011, 18 pages.
International Search Report and Written Opinion of the International Searching Authority PCT/US2010/040075 dated Dec. 1, 2010, 22 pages.
International Search Report and Written Opinion of the International Searching Authority PCT/US2010/040077 dated Nov. 30, 2010, 18 pages.
International Search Report and Written Opinion of the International Searching Authority, PCT/US2011/039907, dated Feb. 16, 2012, 13 pages.
International Search Report and Written Opinion of the International Searching Authority, PCT/US2012/068227, dated Jun. 11, 2014, 12 pages.
International Search Report and Written Opinion of the International Searching Authority, PCT/US2013/037164, dated Sep. 6, 2013, 9 pages.
International Search Report and Written Opinion of the International Searching Authority, PCT/US2015/059922, dated Jan. 8, 2016, 14 pages.
International Search Report and Written Opinion of the International Searching Authority, PCT/US2015/059926, dated Jan. 8, 2016, 12 pages.
International Search Report and Written Opinion of the International Searching Authority, PCT/US2018/012287, dated Apr. 13, 2018, 15 pages.
International Search Report and Written Opinion of the International Searching Authority, PCT/US2018/056228, dated Feb. 12, 2019, 14 pages.
International Search Report and Written Opinion of the International Searching Authority, PCT/US2018/056232, dated Mar. 6, 2019, 13 pages.
International Search Report and Written Opinion of the International Searching Authority, PCT/US2019/044778, dated Oct. 25, 2019, 13 pages.
J. Caelles et al., Anionic and Cationic Compounds in Mixed Systems, Cosmetics & Toiletries, vol. 106, Apr. 1991, pp. 49-54.
J. Crank, The Mathematics of Diffusion, 2nd Edition, 1975, p. 63.
Jing, G. et al., Parallel-META 3: Comprehensive taxonomical and functional analysis platform for efficient comparison of microbial communities, Scientific Reports, 7:40371, DOI: 10.1038/srep40371 (2017), 11 pages.
Jun. 2009 (Jun. 2009). "Tahitian Escape Exfoliating Body Wash", XPOQ2752393, Database accession No. 1124626.
Kikuchi et al., Improvement of Mild Inflammatory Changes of the Facial Skin Induced by Winter Environment with Daily Applications of a Moisturizing Cream. AHalf-Side Test of Biophysical Skin Parameters, Cytokine Expression Pattern and the Formation of Cornified Envelope, Dermatology, vol. 207, No. 3, 2003, pp. 269-275.
KOBO Brochure, Treated Pigments, May 2000.
Kong et al. Performing Skin Microbiome Research: A Method to the Madness. Journal of Investigative Dermatology 2016, vol. 137, pp. 561-568 (Year: 2016).
Kong, et al., Temporal shifts in the skin microbiome associated with disease flares and treatment in children with atopic dermatitis, Genome Research, 2012, 22:850-859, Published by Cold Spring Harbor Laboratory Press.
Mar. 2011 (Mar. 2011), "Healthy Shower Gel", XP002752392. Database accession No. 1513292.
Marzatico et al., Evaluation of anti-wrinkle, elasticizing, ridensifying and skin barrier "repairing" efficacy of a cosmetic treatment, Farcoderm Tested Wellness, BIOTVIA, Jun. 18, 2009, 42 pages.
Meisel et al. Skin Microbiome Surveys are strongly influenced by experimental design. Journal of Investigative Dermatology 2016, vol. 136, pp. 947-946 (Year: 2016).
Michael Starch: "New Cosmetic Ingredients Based on Soybean Oil", IP.com journal, IP.com Inc., West Henrietta NY, US, Jun. 15, 2007, pp. 6, 12, 14.
Milton, Section 9.2: Testing Hypotheses on a Proportion, Introduction to Probability and Statistics, Fourth Edition, Sep. 30, 2002, pp. 129-131.
Niemeyer et al. A systematic literature review of the human skin microbiome as biomarker for dermatological drug development. British Journal of Clinical Pharmacology 2018, vol. 84, pp. 2178-2193 (Year: 2018).
Nov. 2013 (Nov. 2013), "Shampoo", XP002752391, Database accession No. 2242340.

(56) References Cited

OTHER PUBLICATIONS

PCT International Search Report and Written Opinion for PCT/US2008/058556 dated Oct. 22, 2010.
PCT International Search Report and Written Opinion for PCT/US2011/057608 dated Apr. 27, 2012.
PCT International Search Report and Written Opinion for PCT/US2013/033275 dated Mar. 7, 2014.
PCT International Search Report and Written Opinion for PCT/US2013/037165 dated Sep. 12, 2013.
PCT International Search Report and Written Opinion for PCT/US2015/059684; dated Jan. 11, 2016.
Raja K Sivamani et al.: "An Epinephrine-Dependent Mechanism fortheControl of UV-Induced Pigmentation", Journal of Investigative Dermatology, vol. 129, No. 3, Aug. 21, 2008 (Aug. 21, 2008), pp. 784-787.
Rogers et al., Stratum corneum lipids: the effect of ageing and the seasons, Archives of Dermatological Research (1996), 288: 765-770.
Schallreuter et al., The induction of the α-1-adrenoreceptor signal transduction system on human melanocytes, Experimental Dermatology 1996; vol. 5, Issue 1, pp. 20-23.
Seite et al., Barrier function and microbiotic dysbiosis in atopic dermatitis, Clinical, Cosmetic and Investigational Dermatology, vol. 8, 2015, pp. 479-483.
Sep. 2014 (Sep. 2014)"Extra Mild Moisturising Bar", XP0O2752390, Database accession No. 2527423.
Sun et al., A Microbiome-Based Index for Assessing Skin Health and Treatment Effects for Atopic Dermatitis in Children, mSystems, vol. 4, Issue 4, e00293-19, Jul./Aug. 2019.
Tate Owen, Roger Pynn, Jennifer S. Martinez, and Alison Butler; Micelle-to-Vesicle Transition of an Iron-Chelating Microbial Surfactant, Marinobactin E; Nov. 12, 2005; Langmuir, 21,26, 12109-12114 (Year: 2005).
Triethanolamine Product Specification, Chemical Book, 2008.
Two et al. The Cutaneous Microbiome and Aspects of Skin Antimicrobial Defense System Resist Acute Treatment with Topical Skin Cleansers. Journal of Investigative Dermatology 2016, vol. 136, pp. 1950-1954 (Year: 2016).
Van Oss, C.J., Coacervation, Complex Coacervation and Flocculation, Journal of Dispersion Science, vol. 9, 1989.
Vaughan, C. D., Solubility, Effects in Product, Package, Penetration and Preservation, , Cosmetics and Toiletries, vol. 103, Oct. 1988.
Voegeli et al., Efficient and simple quantification of stratum corneum proteins on tape strippings by infrared densitometry, Skin Research and Technology 2007; 13; 242-251.
XP 002332778 "Dove All Day Moisturizing Body Wash" Online URL: http://www.ewg.org/reports/skindeep2/report.php?type=PRODUCT&id=8801874.
Xu et al., Skin benfits of moisturising body wash formulas for children with atopic dermatitis: A randomised controlled clinical study in China, Australasian Journal of Dermatology (2019).
Yogiraj et al. Garica papaya Linn: An overview. International Journal of Herbal Medicine 2014, vol. 2, No. 5, pp. 01-08 (Year: 2014).
"Effects of xerosis and aging on epidermal proliferation and differentiation", Br. J. Dermatology, 137: 219-225 (1997) M. Engelke.
"The validity and practicality of sun-reactive skin types I through VI". Arch. Dermatology, 124: 869-871 (1988).
Draelos "The effect of Cetaphil Gentle Skin Cleanser on the skin barrier of patients with rosacea". Cutis Apr. 2006, 77 (4Suppl), 2006, pp. 27-33.
Joseph Fowler, Understanding the role of Natural Moisturizing Factor in Skin Hydration, Jul. 2012, pp. 36-40.
Maeno et al., Direct quantitative analysis of the natural moisturizing factor (NMF) in the stratum corneum by direct analysis in real time mass spectrometry (DART- MS), Jul. 2017, vol. 9, pp. 4851-4857.
Seite et al. "Using a specific cleanser for patients with mild atopic dermatitis: relationship between clinical efficacy and skin microbiota modification". SKIN The Journal of Cutaneous Medicine 2017, 1, 44, 10.25251/skin.1.supp.43, 3 pages.

\* cited by examiner

AEROSOL FOAM SKIN CLEANSER

FIELD OF THE INVENTION

A packaged aerosol foaming skin cleanser can include a multiphase skin cleansing composition, a low pressure foaming agent, and a package.

BACKGROUND OF THE INVENTION

Foam cleansers are becoming a popular form among consumers. Foaming cleansers are often micellar with a low viscosity to allow for easy foaming of the product. These thin, micellar compositions, while useful for cleansing, are not the best vehicle for delivery of benefit agents to the skin during the cleansing process. As such, there is a need for an aerosol foam skin cleanser which has the ability to deliver benefit agents to the skin.

SUMMARY OF THE INVENTION

A packaged aerosol foaming skin cleanser, comprising: a) a multiphase skin cleansing composition, comprising a structured surfactant phase and a benefit phase, wherein the structured surfactant phase comprises a branched structured surfactant, and the benefit phase comprises a hydrophobic benefit agent; wherein the multiphase cleansing composition is shear thinning and has a viscosity of about 8,000 cps to about 80,000 cps; b) a low pressure foaming agent; and c) a package.

This and other possible combinations will be explained in more detail below.

DETAILED DESCRIPTION OF THE INVENTION

Figure 1:
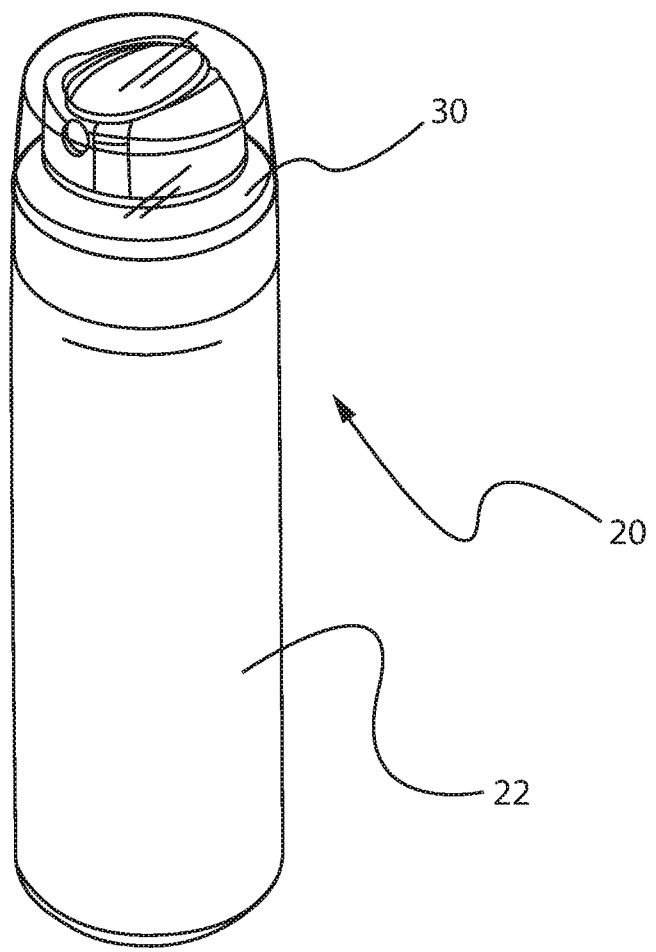
FIG. 1 is a perspective view of an aerosol package.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

"Foaming agent," as used herein, refers to a material which is intermingled with a skin cleansing composition inside an aerosol package and results in the skin cleansing composition foaming upon or shortly after exiting an aerosol package.

"Free of," as used herein, means the stated ingredient has not been added to the aerosol foam skin cleanser, but may incidentally form as a by-product or reaction product of the other components.

"Low pressure foaming agent," as used herein, refers to a foaming agent with a vapor pressure of about 20 psi or less at a temperature of 21° C. which can be measured using a standard pressure gauge and method on the foaming agent in its canister before addition to an aerosol foam skin cleanser.

"Low pressure propellant," as used herein, refers to a propellant with a vapor pressure of about 20 psi or less at a temperature of 21° C. which can be measured using a standard pressure gauge and method on the foaming agent in its canister before addition to an aerosol foam skin cleanser.

"Multiphase," when used with respect to skin cleansing compositions, refers to skin cleansing compositions comprising at least two chemically distinct phases (e.g., a structured cleansing phase and a benefit phase). Such phases can be in direct physical contact with one another. The phases of a multiphase skin cleansing composition can be blended or mixed to a significant degree, but still be physically distinct, like a dispersion. In these situations, the physical distinctiveness is often undetectable to the naked eye. When in a blended state, the phases are stable and do not significantly phase separate while sitting undisturbed. By no significant phase separation is meant that the composition does not need to be shaken prior to use. In addition, in the blended configuration, the phases are not in the form of an emulsion. The phases may also be in physical contact and visually distinct. Visually distinct phases can take many forms (e.g., phases can appear as striped, marbled). Again, visually distinct phases are stable, not phases that have separated upon standing and then need to be redispersed prior to use. The skin cleansing composition can also include a combination blended and visually distinct phases.

"Non-ionic low HLB Emulsifiers," as used herein, refers to non-ionic surfactants with HLB (hydrophilic and lipophilic balance) values from about 1.5 to about 13.

"Propellant," as used herein, refers to a material which helps to expel a skin cleansing composition from an aerosol package, but does not interact with the skin cleansing composition until dispensing from the aerosol package.

"STnS" refers to sodium trideceth(n) sulfate, wherein n can define the average number of moles of ethoxylate per molecule.

"Structured" as used herein with respect to a composition or a phase, means having a rheology that confers stability on the multiphase composition. The degree of structure is determined by characteristics determined by one or more of the following methods: the Young's Modulus Method, Yield Stress Method, or the Zero Shear Viscosity Method, all in the Test Methods section below. Accordingly, a surfactant phase is considered to be structured, if the phase has one or more of the following characteristics: a Yield Stress of greater than about 0.1 Pascal (Pa) to about 300 Pa; a Zero Shear Viscosity of at least about 500 Pascal-seconds (Pa-s) to about 10,000 Pa-s; and/or a Young's Modulus of greater than about 1 Pascal (Pa) to about 300 Pa.

Aerosol Foam Skin Cleanser

Skin cleansers can come in many forms. A form that is gaining in popularity is that of a foam. Foam skin cleansers may be dispensed as a foam or may foam after dispensing. Foaming skin cleansers are generally micellar compositions which are low in viscosity which is usually less than 8,000 cps, which allows for easy dispensing and foaming of the cleanser. In addition, the low viscosity allows for the use of mechanical foamers, like pump foamers, in addition to aerosol foamers.

These thin, micellar compositions, while useful for cleansing, are not the best vehicle for delivery of benefit agents to the skin during the cleansing process. When looking to both cleanse and deliver benefit agents to the skin, structured multiphase compositions are good candidates, like those containing a lamellar phase. Lamellar phase containing compositions, however, are not seen as ideal for foaming. The structure of these compositions usually results in a higher viscosity, above 8,000 cps. Both the structure and the viscosity can make these compositions difficult to foam. In addition, since the structure helps with the delivery of benefit agents to the skin, it is ideal to maintain the structure of the composition even after addition of a propellant or foaming agent.

Compositions can be structured in multiple ways. The most common way to structure a composition is through the use of non-surfactant structurants. These materials often consist of larger chain fatty acids or their esters or larger chain fatty alcohols or their ethers. These types of structurants, however, form a more rigid structure which may require high pressure propellant for easy dispensing from the aerosol container. The high pressure propellant causes safety concerns when distributing the aerosol products at high temperature regions. Therefore, there is a need to develop a structured surfactant which can be dispensed with a low pressure foaming agent.

One way to overcome the negatives associated with the use of non-surfactant structurants is to utilize structured surfactants, especially in combination with low HLB non-ionic emulsifiers. Structured surfactants with low HLB non-ionic emulsifiers tend to have optimum rheology and compatibility with a low pressure foaming agent. Even within the structured surfactant family, there are some materials which are better suited for use with an aerosol foam skin cleanser. These include, for example, structured surfactants which are branched anionic surfactants.

Another factor for consideration is the level of pressure in the package. Aerosol products have strict guidelines due to the pressurized nature of the material with the package and the ability of such packages to rupture if the pressure inside the package becomes too high. This can happen, for example, with an increase in external temperature during transport. The high viscosity of structured compositions would lead one to consider the use of higher pressure propellants and/or foaming agents (vapor pressure of about 25 psi or more at 21° C.) for dispensing of the product to overcome the viscosity hurdle of the composition itself. However, utilizing these higher pressure propellants and/or foaming agents can be limiting from a distribution standpoint due to the concerns of the package pressure becoming too high during transport and/or storage.

Another drawback of the use of high pressure propellants and/or foaming agents is the harshness of such high pressure on the compositions themselves during dispensing. The use of higher pressure propellants and/or foaming agents can place limits on the ingredients which can be used within the formulations. High pressure propellants and/or foaming agents can also work to decrease the density of the product after foaming which can negatively impact the ability of the composition to deposit benefit agents to the skin. One hypothesis is that the high pressure foaming agent and/or propellant can partition into the benefit phase in the packaged product. Upon dispending the product, the foaming agent and/or propellant quickly evaporates into the gas state and may result in smaller particles of the benefit phase comprising the benefit agents. The smaller particles of the benefit phase comprising the benefit agent could lead to lower deposition of the benefit agent on skin.

In addition, a high pressure foaming agent creates a low density, low yield stress foam that has the feeling of air upon use and disappears quickly upon lathering. A low pressure foaming agent creates a slow-releasing foam that initially looks like liquid, but when shear is applied, quickly generates denser, higher yield stress, and more stable foam.

One of the factors which are believed to help allow for the use of a low pressure foaming agent and/or propellant is the rheology characteristics of the composition. The preferred rheology for the use of a low pressure foaming agent is as below: a Yield Stress of from about 0.1 Pascal (Pa) to about 300 Pa, from about 0.5 Pa to about 200 Pa, from about 1.0 Pa to about 150 Pa, from about 2.0 Pa to about 100 Pa, from about 5 Pa to about 50 Pa, or from about 10 Pa to about 50 Pa as measured by the Yield Stress Method; a Zero Shear Viscosity of about 500 Pascal-seconds (Pa-s) to about 10,000 Pa-s, about 1,000 Pa-s to about 5,000 Pa-s, or about 1,500 Pa-s to about 5,000 Pa-s; and/or a Young's Modulus of from about 1 Pascal (Pa) to about 300 Pa, from about 5 Pa to about 200 Pa, from about 10 Pa to about 150 Pa, or from about 20 Pa to about 120 Pa.

Aerosol Foam Skin Cleanser

An aerosol foam skin cleanser can include a package, a low pressure foaming agent, and a skin cleansing composition. The package is any that is suitable to foaming a multiphase skin cleansing composition, for example, an aerosol package. A low pressure foaming agent includes those foaming agents and blends which have a vapor pressure of about 20 psi or less at 21° C. The aerosol foam skin cleanser may also comprise a low pressure propellant. A low pressure foaming agent includes those foaming agents and blends which have a vapor pressure of about 20 psi or less at 21° C. An aerosol foam skin cleanser can include from about 85 to about 99, by weight of the aerosol foam skin cleanser of a skin cleansing composition, and from about 1% to about 15%, by weight of the aerosol foam skin cleanser, of a low pressure foaming agent and/or low pressure propellant.

a) Skin Cleansing Composition

A skin cleansing composition can be multiphase, for example, the skin cleansing composition may include a cleansing phase and a benefit phase. The cleansing phase and the benefit phase may be in physical contact. A skin cleansing composition may include a combination of multiple phases. A skin cleansing composition may comprise from about 50% to about 99%, by weight of the composition, of a cleansing phase, and from about 1% to about 50%, by weight of the composition, of a benefit phase. The skin cleansing composition may be structured. The skin cleansing composition may also be shear thinning.

i) Cleansing Phase

A cleansing phase can be structured. The structure may include, for example, a lamellar structure or phase. A cleansing phase can include a primary surfactant. The primary surfactant can include a branched anionic surfactant. The primary surfactant can be a structured surfactant. The structured surfactant can include a branched anionic surfactant. A cleansing phase can include, for example, from about 5% to about 30%, or from about 5% to about 25%, by weight of the skin cleansing composition, of a total surfactant. A cleansing phase may include, for example, from about 5% to about 30%, from about 7% to about 25%, or from about 8% to about 22%, by weight of the skin cleansing composition, of a primary surfactant. Structured surfactants can include, for example, sodium trideceth(n) sulfate (STnS).

For STnS, n defines the average moles of ethoxylation. n can range from about 0.5 to about 2.7, from about 1.1 to about 2.5, from about 1.8 to about 2.2, or n can be about 2. When n is less than 3, STnS can provide improved stability, improved compatibility of benefit agents within the skin cleansing compositions, and increased mildness of the skin cleansing composition.

In addition to the primary surfactant, a skin cleansing composition may comprise a co-surfactant. A skin cleansing composition can include from about 1% to about 20%, by weight of the skin cleansing composition, of a co-surfactant. The co-surfactant can include, for example, anionic and zwitterionic surfactants, and non-ionic surfactants.

Examples of some suitable anionic co-surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, sodium cocoyl isethionate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Amphoteric co-surfactants can include those that can be broadly described as derivatives of aliphatic secondary and tertiary amines in which an aliphatic radical can be a straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate, N-higher alkyl aspartic acids, and combinations thereof. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic co-surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

A cleansing phase can comprise a nonionic emulsifier. The nonionic emulsifier may be a low HLB emulsifier. A low HLB non-ionic emulsifier has an HLB from about 1.5 to 13.0, from about 3.4 to 13.0, from about 3.4 to about 9.5, or from about 3.4 to about 8.0. The skin cleansing composition can comprise a nonionic emulsifier at concentrations ranging from about 0.1% to about 10%, from about 0.25% to about 8%, from about 0.5% to about 5%, from about 1.0% to about 3%, or from about 1.5% to about 2.5%, by weight of the skin cleansing composition.

The balance between the hydrophilic and lipophilic moieties in a surfactant molecule is used as a method of classification (hydrophile-lipophile balance, HLB). The HLB values for commonly-used surfactants are readily available in the literature (e.g., HLB Index in *McCutcheon's Emulsifiers and Detergents*, MC Publishing Co., 2004). For example, cocamide monoethanolamine (CMEA) is known in the art to have an HLB value of 16.8. If no value is shown in the literature, an HLB value may be estimated by calculation. The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20.

Non-limiting examples of nonionic emulsifiers for use herein can comprise glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, or mixtures thereof.

A cleansing phase may also comprise an associative polymer. The cleansing phase can comprise from about 0.001% to about 5%, from about 0.005% to about 0.5%, from about 0.007% to about 0.05%, from about 0.008% to about 0.04%, or from about 0.01% to about 0.03%, by weight of the personal care composition, of an associative polymer.

Such associative polymers can be crosslinked, alkali swellable, associative polymers comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in the presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains.

It has also been discovered that crosslinked, associative polymers having certain % HM and certain carbon numbers of hydrophobic end groups of alkyl side chains can provide significant enhancement of structure to skin cleansing compositions comprising a structured surfactant, especially to skin cleansing compositions comprising reduced levels of surfactant. Such associative polymers can also provide the above structure at low levels. Concentrations of associative polymers of about 5% or even 10% have been known to provide a sufficient amount structure. It has been discovered that when an associative polymer % HM and an alkyl side chain number of carbons can be optimized, the structure of a cleansing phase can be increased using less than about 3 wt %, less than about 2%, less than about 1%, and less than about 0.2%, of an associative polymer, as a weight percentage of the cleansing phase.

The acidic monomer can comprise any acid functional group, for example sulfate, sulfonate, carboxylate, phosphonate, or phosphate or mixtures of acid groups. The acidic monomer can comprise, for example, a carboxylate. Alternatively, the acidic monomer can be an acrylate, including acrylic acid and/or methacrylic acid. The acidic monomer can comprise a polymerizable structure, e.g., vinyl functionality. Mixtures of acidic monomers, for example acrylic acid and methacrylic acid monomer mixtures, may be useful as well.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (cetyl) alkyl hydrophobic side chains with about 0.7% hydrophobic modification, but a percentage hydrophobic modification can be up to an aqueous solubility limit in surfactant containing compositions (e.g., up to 2%, 5%, or 10%). Other associative polymers can include stearyl, octyl, decyl, and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

A skin cleansing composition may also comprise a non-associative polymer. The skin cleansing composition can comprise from about 0.01% to about 5%, from about 0.05% to about 1%, from about 0.07% to about 0.5%, or from about 0.1% to about 0.3%, by weight of the skin cleansing composition, of a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), synthetic hydrocarbon polymers (e.g., polyacrylamide and copolymers, polyethylene oxide, polyacrylic acid copolymers), and combinations thereof.

A skin cleansing composition can also comprise a cationic deposition polymer. The cationic deposition polymer can be present in an amount of 0.1% to about 2%, by weight of the skin cleansing composition. Suitable cationic deposition polymers can contain cationic nitrogen-containing moieties such as quaternary moieties. Non-limiting examples of cationic deposition polymers can include polysaccharide polymers, such as cationic cellulose derivatives. Cationic cellulose polymers can be salts of hydroxyethyl cellulose reacted with trimethyl ammonium substituted epoxide, referred to in the industry (CTFA) as Polyquaternium 10, which can be available from Amerchol Corp. (Edison, N.J.) in their Polymer KG, JR, and LR series of polymers. Other suitable cationic deposition polymers can include cationic guar gum derivatives, such as guar hydroxypropyltrimonium chloride, specific examples of which can include the Jaguar® series commercially available from Rhodia Inc. and N-Hance® polymer series commercially available from Aqualon. Deposition polymers can have a cationic charge density from about 0.8 meq/g to about 2.0 meq/g or from about 1.0 meq/g to about 1.5 meq/g, or about 0.96 meq/g.

A cleansing phase may also include an electrolyte. Electrolytes may be present at a level of about 1% to about 10%, by weight of the skin cleansing composition. Suitable electrolytes can include anions such as phosphate, chloride, sulfate, citrate, and mixtures thereof and cations such as sodium, ammonium, potassium, magnesium, and mixtures thereof. For example, suitable electrolytes can include sodium chloride, ammonium chloride, sodium sulfate, ammonium sulfate, and mixtures thereof.

A cleansing phase may include water. The cleansing phase can comprise from about 10% to about 90%, from about 40% to about 85%, or from about 60% to about 80%, by weight of the skin cleansing composition, of water.

ii) Benefit Phase

A skin cleansing composition may also comprise a benefit phase. The skin cleansing compositions can include two or more benefit phases. A benefit phase can be hydrophobic and/or anhydrous. A benefit phase can also be substantially free of or free of surfactant. A skin cleansing composition may include from about 3% to about 50%, by weight of the skin cleansing composition, of a benefit phase. Usually, the benefit phase is dispersed in the cleansing phase.

A benefit phase can comprise a hydrophobic benefit agent. A skin cleansing composition may include from about 0.1% to about 20%, by weight of the skin cleansing composition, of a hydrophobic benefit agent. A hydrophobic benefit agent can be insoluble in the cleansing phase. Suitable benefit agents can include, for example, petrolatum, monoglyceryl monooleate, mineral oil, glycerides (e.g., soybean oil), sucrose polyesters, lanolin, lanolin derivatives, lanolin esters, lanolin oil, natural waxes, synthetic waxes, volatile organosiloxanes, derivatives of volatile organosiloxanes, non-volatile organosiloxanes, derivatives of non-volatile organosiloxanes, natural triglycerides, synthetic triglycerides, and mixtures thereof.

SEFOSE® includes one or more types of sucrose polyesters. Sucrose polyesters are derived from a natural resource and therefore, the use of sucrose polyesters as the benefit agent can result in a positive environmental impact. Sucrose polyesters are polyester materials having multiple substitution positions around the sucrose backbone coupled with the chain length, saturation, and derivation variables of the fatty chains. Such sucrose polyesters can have an esterification ("IBAR") of greater than about 5. For example, the sucrose polyester may have an IBAR of about 5 to about 8. In another example, the sucrose polyester may have an IBAR of about 5-7; in another example, the sucrose polyester can have an IBAR of about 6. In yet another example, the sucrose polyester can have an IBAR of about 8. As sucrose polyesters can be derived from natural resources, a distribution in the IBAR and chain length may exist. For example, a sucrose polyester having an IBAR of 6 may contain a mixture of mostly IBAR of about 6, with some IBAR of about 5, and some IBAR of about 7. Additionally, such sucrose polyesters may have a saturation or iodine value ("IV") of about 3 to about 140. In another example, the sucrose polyester may have an IV of about 10 to about 120. In yet another example, the sucrose polyester may have an IV of about 20 to 100. Further, such sucrose polyesters may have a chain length of about $C_{12}$ to $C_{20}$.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio. Sucrose polyesters can also be combined with other benefit agents in the benefit phase.

Non-limiting examples of glycerides suitable for use as hydrophobic benefit agents herein can include castor oil, safflower oil, corn oil, walnut oil, peanut oil, olive oil, cod liver oil, almond oil, avocado oil, palm oil, sesame oil, soybean oil, vegetable oils, sunflower seed oil, vegetable oil derivatives, coconut oil and derivatized coconut oil, cottonseed oil and derivatized cottonseed oil, jojoba oil, cocoa butter, petrolatum, mineral oil, and combinations thereof.

Non-limiting examples of alkyl esters suitable for use as hydrophobic benefit agents herein can include isopropyl esters of fatty acids and long chain esters of long chain (i.e. $C_{10}$-$C_{24}$) fatty acids, e.g., cetyl ricinoleate, non-limiting examples of which can include isopropyl palmitate, isopropyl myristate, cetyl riconoleate, and stearyl riconoleate. Other examples can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic benefit agents herein can include oleyl myristate, oleyl stearate, oleyl oleate, and combinations thereof.

Non-limiting examples of polyglycerin fatty acid esters suitable for use as hydrophobic benefit agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic benefit agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic benefit agents herein can include dimethicone copolyol, dimethylpolysiloxane, diethylpolysiloxane, mixed $C_1$-$C_{30}$ alkyl polysiloxanes, phenyl dimethicone, dimethiconol, and combinations thereof. Still other suitable hydrophobic skin benefit agents can include milk triglycerides (e.g., hydroxylated milk glyceride) and polyol fatty acid polyesters.

iii) Other Skin Cleansing Composition Materials

In addition to what has been described above, a skin cleansing may also include additional materials in any phase. These materials can include for example, perfume, colorants, antimicrobials, pH modifiers, and the like. Such materials are usually formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less by weight of the personal care composition.

b) Low Pressure Foaming Agent

An aerosol foam skin cleanser can include a low pressure foaming agent. The low pressure foaming agent can be a hydrocarbon foaming agent. The total amount of foaming agent that is part of the aerosol foam skin cleanser can range from about 1% to about 20%, by weight of the aerosol foam skin cleanser.

Suitable hydrocarbon foaming agents can include those which have a vapor pressure of about 20 psi or less at 21° C. For example, this could include n-butane, an isobutane blend, isopentane, compressed gases such as carbon dioxide, nitrous oxide, nitrogen, compressed air, or a combination thereof. n-butane has a vapor pressure of about 17 psi when measured at 21° C. An isobutene blend can include, for example, a combination of isobutane and isopentane with about 25 weight percent of the isobutane and about 75 weight percent of the isopentane, by weight of the blend. This blend has a vapor pressure of about 7 psi at a temperature of 21° C.

The low pressure foaming agent for use in the aerosol foam skin cleanser can also be selected from the group consisting of halogenated alkenes of generic formula that would include numerous HFOs and HCFOs. In addition, the foaming agent listed can be mixed with one or more hydrofluoroolefins (HFOs), hydrochlorofluoroolefins (HCFOs), hydrofluorocarbons (FFCs), chlorofluorocarbons (CFCs), hydrocarbons, alkyl ethers, and compressed gases. For example, the low pressure foaming agent can comprise trans-1-chloro-3,3,3-trifluoropropene (Solstice® HCFO-1233zd), from Honeywell with a vapor pressure of about 16.3 psi at 21° C.

c) Low Pressure Propellant

The aerosol foam skin cleanser may also comprise a low pressure propellant. A low pressure propellant may include any of those described above as a low pressure foaming agent. A low pressure propellant may be present at a level of about 1% to about 20%, by weight of the aerosol foam skin cleanser.

In some processes, like the bag on valve process, propellant is injected into the canister package during the crimping process as the driving force to compress a bag that is attached to the valve. This process is called "pressure crimping". Pressure crimping can be accomplished using the technology of under-the-cup gassing. Thus, in some cases, instead of inputting a particular amount of propellant in the package, the target is a pressure. For low pressure applications, as discussed herein, the target pressure would be 20 psi or less at a temperature of 21° C. The package could be filled with a propellant to a pressure of about 11 to about 15 psi.

d) Aerosol Package

The aerosol foam skin cleanser may be included in any suitable type of aerosol package 20, see FIG. 1. An aerosol package can include a container body 22 and a cap 30. An aerosol package can be, for example, in a dip tube configuration (see FIG. 2B) or a bag in bottle configuration, like the bag on valve configuration (see FIG. 2A).

In either the dip tube or the bag on valve configuration, the aerosol package 20 may have a cap 30, a valve assembly 28 attached to at least a portion of the cap 30, a valve cup 26 which may be attached to the neck 24 of the container body 22 and to the valve assembly 28.

Figures 2A, 2B:
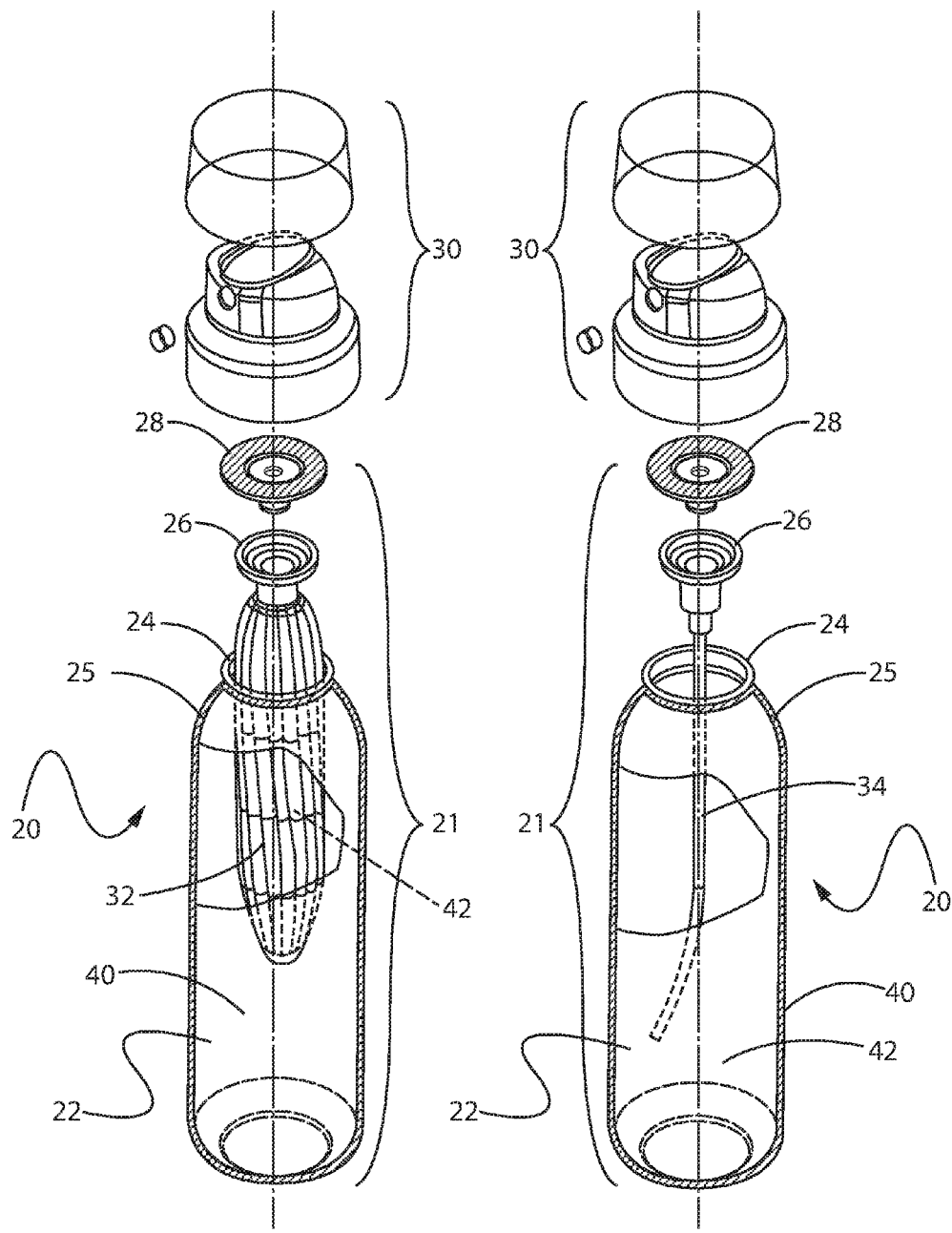
FIG. 2A is an exploded view of the aerosol package of FIG. 1 having a bag on valve configuration.
FIG. 2B is an exploded view of the aerosol package of FIG. 1 having a dip tube configuration.

In the bag on valve configuration of FIG. 2A, a collapsible bag 32 may be attached to the valve cup 26 and contain an aerosol foam skin cleanser 42. A propellant 40, may be contained between the collapsible bag 32 and the exterior wall 25 of the container body 22.

In the dip tube configuration of FIG. 2B, a dip tube 34 can be attached to a valve cup 26 and reside inside the container body 22 in contact with an aerosol foam skin cleanser 42.

e) Test Methods a. T-Bar Viscosity Method

The viscosity of a skin cleansing composition can be assessed by the T-Bar Viscosity Method. The apparatus for T-Bar measurements includes a Brookfield DV-II+ Pro Viscometer with Helipath Accessory; a chuck, weight and closer assembly for T-bar attachment; a T-bar Spindle D, a personal computer with Rheocalc software from Brookfield, and a cable connecting a Brookfield Viscometer to a computer. First, weigh 80 grams of a skin cleansing composition in a 4-oz. glass jar. Measure a T-bar viscosity by carefully dropping the T-Bar Spindle to an interior bottom of the glass jar and set the Helipath stand to travel in an upward direction. Open the Rheocalc software and set the following data acquisition parameters: Speed to 5 rpm, Time Wait for Torque to 00:01 (1 second), and Loop Start Count to 100. Start data acquisition and turn on the Helipath stand to travel upward at a speed of 22 mm/minute. The T-Bar viscosity is an average T-Bar viscosity reading between the $10^{th}$ reading and the $90^{th}$ reading (the first ten readings and the last ten readings are not used for the average T-Bar viscosity calculation). The T-Bar viscosity reading is provided in cP.

b. Yield Stress, Young's Modulus, and Zero Shear Viscosity Methods

The Zero Shear Viscosity of a material which is a phase or a component of the skin cleansing composition, can be measured either prior to combining in the skin cleansing composition, after preparing a composition, or first separating a phase or component from a personal care composition by suitable physical separation means, such as centrifugation, pipetting, cutting away mechanically, rinsing, filtering, or other separation means. The timing of the measurement can depend on what is available. For example, if a final product is all that is available and a phase of the product is the target for measurement, then the phase will be separated prior to measurement.

A controlled stress rheometer such as a TA Instruments AR2000 Rheometer is used to determine the Yield Stress and Zero Shear Viscosity. The determination is performed at 25° C. with a 4 cm diameter parallel plate measuring system and a 1 mm gap. The geometry has a shear stress factor of 79580 m-3 to convert torque obtained to stress. Serrated plates can be used to obtain consistent results when slip occurs.

First, the target material is positioned on a rheometer base plate; the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset which can influence the results obtained. If the material comprises particles discernible to the eye or by feel (e.g., beads) that are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty measurement points per decade of stress increase are obtained. Stress, strain, and viscosity are recorded. If the measurement result is incomplete, for example, if material is observed to flow from the gap, results obtained are evaluated with incomplete data points excluded. If there are insufficient points to obtain an accurate measurement, the measurement is repeated with increased number of sample points.

The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m*\text{Log(stress)} + b \qquad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., 10.sup.x for each x). The predicted strain is compared to the actual strain at each measurement point to obtain a % variation at each point, using Equation (2).

$$\% \text{ variation} = 100*(\text{measured strain} - \text{predicted strain})/\text{measured strain} \qquad (2)$$

The Yield Stress is the first stress (Pa) at which % variation exceeds 10% and subsequent (higher) stresses result in even greater variation than 10% due to the onset of flow or deformation of the structure.

The Young's Modulus (Pa) is obtained by graphing Stress (Pa) vs. Strain (unitless) and obtaining a slope of a regression line of an initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-s) for viscosity data obtained between and including 0.1 Pa and a point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

As set forth above, a phase or composition can be considered to be structured if it has a Zero Shear Viscosity of about 500 Pascal-seconds (Pa-s) to about 10,000 Pa-s, a Yield Stress of greater than about 0.1 Pascal (Pa) to about 300 Pa, and/or a Young's Modulus of greater than about 1 Pascal (Pa) to about 300 Pa.

c. Benefit Agent Deposition Method

The amount of deposition of a benefit agent can be measured in vitro. The In-Vitro deposition method measures the deposition of benefit agents on a mechanically stressed skin mimic. The method compares spectral data of the skin mimic surface material before and after cleansing in an automated cleansing unit.

The In-Vitro deposition method uses two 96-well microplates (hereinafter referred to as "microplates"). Suitable 96-well microplates are commercially available from PerkinElmer and from VWR.com. For example, the SpectraPlate 96-MG from PerkinElmer has 8 rows and 12 columns with a well volume of 400 .mu.l. The SpectraPlate 96-MG comprises the approximate dimensions of 14.6 mm in height, 127.8 mm in length and 85.5 mm in width. The SpectraPlate 96-MG has a well diameter of 7.15 mm, a well depth of 10.8 and a well to well spacing of 9.0 mm A 96-well microplate is provided for containing the samples to be measured.

The in-vitro deposition method uses approximately 1536 bodies. Each body is approximately 2 mm in circumference spherical stainless steel bearings that comprise ferrometallic material, such as those available from WLB Antriebeselemente Gmbh, Scarrastrasse 12, D-68307 Mannheim, Germany Eight bodies carefully loaded into each of the 96 wells of microplates to ensure the same number is loaded into each well.

Before samples are prepared, the skin cleansing compositions are prepared according to the description in the Example Section below. After the examples of the personal care compositions are prepared, samples are prepared by combining a personal care composition and distilled water. For each sample, 90+\−0.02 grams of distilled water is dispensed into a mixing vessel. The mixing vessel is secured to the base of a mixer, such as a table top mixer from IKA, the mixer blades are adjusted into the distilled water within the mixing vessel. A syringe is then zeroed on a balance. The syringe is filled with the designated skin cleansing composition. The syringe is weighed and small amounts of the designated skin cleansing composition are dispensed until 10 grams of the skin cleansing composition remains in the syringe. The mixer is turned on at a speed of 500 rpm and the contents of the syringe are dispensed into distilled water within the mixing vessel. The distilled water and the designated skin cleansing composition are mixed for 2 minutes at 500 rpm forming the sample. The sample is withdrawn by syringe from the mixing vessel while the mixer is on at a speed of 300 rpm. The mixing and dispensing procedures are followed for mixing and dispensing for the control sample and the test samples 1-5. After the samples are prepared, the control samples and test samples are dispensed in the specified wells of the microplate.

The skin mimic used in the in-vitro deposition methods is comprised of a molded bicomponent polyethylene substrate. The skin mimic is textured on one side with a pattern that resembles the texture of human skin. The textured side of the skin mimic is coated with 1,1,1-trimethyl-1-pentene that is plasma deposited. The skin mimic has a total surface energy of 32+/−1.0 (mJ/m$^2$), a zeta potential of (−) 27.4 (mV), a contact angle in water of 100° F.+/−2.0.

The preparation of the skin mimic comprises the steps of preparing the metallic mold (a), forming the substrate of the skin mimic (b) and formation of the treated test mimic of the skin mimic.

(a) Metallic Mold Preparation: A pattern resembling the texture of human forearm skin is formed from a photograph image of human forearm skin. The pattern is transferred to a clear sheet to form a mask. A DuPont® MX series dry film photoresists is adhered to the metal sheet. The mask is placed on top of the metal sheet to form a metal/photoresist/mask. The composite of metal/photoresist/mask is exposed to an appropriate dose of UV light, using industry standard exposure tools. The mask is removed, the photoresist is developed and the metal sheet is etched using appropriate etching solutions, as described in standard textbooks on second level microelectronics packaging, for example, Donald Seraphim, Ronald Lasky and Che-Yu Li, Principles of Electronic Packaging, Mc-Graw Hill Inc. (1989).

(b) Formation of the Substrate of the Skin Mimic: A 1:1 mixture of Skin-Flex SC-89 Stretch-paint and Skin-Flex SC-89 Thinner S4 SC-89 Thinner, both available from Burman Industries, (Van Nuys, Calif.) is poured into the prepared metallic mold and allowed to dry overnight. The amount of the mixture poured is adjusted according to the size of the mold, to yield a final substrate that is typically between 600 to 800 micrometers thick. After overnight drying, the substrate material is carefully peeled off of the metallic mold.

(c) Formation of the treated test region of skin mimic. The plasma deposition is performed in a plasma unit, between the two electrodes, by application of the continuous wave radiofrequency (hereinafter referred to as "RF") power. The effective plasma treatment area is approximately 40 cm by 20 cm. The plasma unit comprises a cylindrical vacuum chamber having a diameter of approximately 30.5 cm and a length of 61.0 cm. Vacuum is produced by means of a LEYBOLD® PCS 25 vacuum pump. The RF energy is supplied from a PE 1000 ADVANCED ENERGY®40 KHz power supply, across a set of parallel aluminum electrodes in the vacuum chamber.

The substrate is placed on a perforated aluminum sample tray in between parallel plate aluminum electrodes in the vacuum chamber and the vacuum chamber pressure is reduced to approximately 100 milliTorr (mTorr). The substrate to be plasma coated is substantially degassed by adding a mixture of argon and nitrogen gas into the vacuum chamber at flow rates of 20 sccm of argon and 10 sccm of nitrogen, (where "sccm" means standard cubic centimeter per minute) for about one hour. After the substrate is degassed for one hour, the vacuum chamber pressure is reduced to 10 mTorr and 25 W of continuous wave RF power is applied for approximately 5 minutes while allowing the argon/nitrogen gas mixture to flow into the vacuum chamber at flow rates of 20 sccm of argon and 10 sccm of nitrogen. After 5 minutes, the release of gas is stopped and vacuum chamber is evacuated to the pressure of 10 mTorr. The 1,1,1-trimethyl-1-pentene coating material available from Aldrich is introduced into the vacuum chamber to a pressure of 100 mTorr at a flow rate selected is from about 10 sccm to 200 sccm depending the knowledge of or may be determined with limited experimentation by one of ordinary skill in the art. While the coating material is introduced into the vacuum chamber 25 W of continuous wave RF power is applied for approximately 25 minutes while maintaining a vapor pressure of approximately 100-120 mTorr. The plasma deposition results in a polymeric coating of 1,1,1-trimethyl-1-pentene that is covalently bonded to the substrate. The exact times for plasma deposition will be within the knowledge or may be determined with limited experimentation by one of skill in the art. After 25 minutes, the power to the plasma unit is turned off and the flow of the coating material is stopped. The vacuum chamber is purged with about 20 sccm argon for about 30 min prior to the removal of the coated substrate. The plasma coated substrates are removed from the chamber the contact angle, the surface charge and the thickness of the coating layer is determined by video contact angle measurement system (VCA-2500 from ASM), zeta-potential measurement (Anton Parr Electrokinetic Analyzer, Model BI-EKA) and Atomic Force Microscopy (Q-Scope 250 from Quesant Corporation) methods. However, one of skill in the art will understand that a variety of coating materials, as described herein, may be used, the choice of which will be determined by the surface property of the keratinous tissue that one desires to reproduce.

After all of the wells of the microplate are filled with the samples and the pieces of skin are made and coated, the skin mimic is prepared for the in vitro deposition method. Two pieces of skin mimic are prepared by cutting the skin mimic to fit on top of the openings of the wells of the microplate while wearing gloves. The two pieces of skin mimic pieces are numbered "1" and "2".

A base line spectral data was obtained by the spectrophotometer for both pieces of skin mimic. An Eye-one® IO Spectrophotometer from GretagMacbeth with Measure Tool Software (collectively hereinafter referred to as "spectrophotometer") and a computer associated with the spectrophotometer (hereinafter referred to as "computer") was utilized. The reading surface of the spectrophotometer is cleaned prior to each reading. The reading surface of the spectrophotometer is black in order to provide adequate reflection. The first piece of skin mimic is placed on the reading surface with the textured and treated region of the skin mimic facing the spectrophotometer. Next, a piece of plastic having a plurality of holes which correspond in size to the openings of the microplate is placed over the textured and treated region of the skin mimic A scan is then performed using the robot arm of the spectrophotometer. The baseline spectral data for the first piece of skin mimic is saved on a computer as the first baseline. The reading surface of the spectrophotometer is cleaned and the spectral data for the second piece of skin mimic surface is, as described for the first piece of skin mimic. The baseline spectral data for the second piece of skin mimic is saved on the computer as the second baseline.

Next, the pieces of skin mimics are arranged over the openings of the wells of the microplates. The pieces of skin mimic surface material are transferred to cover the openings of the wells of the each of the microplates to ensure that the textured and treated region of the skin mimic is facing the openings of the wells of the microplate. A lid is placed over each piece of the skin mimic and the associated microplate to form a lidded microplate.

The next step is to place the lidded microplates into the microplate holders 20 of automated cleansing unit. The automated cleansing unit comprises a horizontal base comprising four microplate holders. The horizontal base is made of rectangle of aluminum comprising the following approximate dimensions of ⅜ inch in height, fourteen inches in width and twenty seven inches in length. The automated cleansing unit comprises two vertical supports comprised of aluminum with the approximate dimensions of one inch by two inches by ten and ¾ of an inch in height. The vertical supports are attached to a horizontal support comprising a rodless air slide. The horizontal support comprising a rodless air slide comprises the approximately dimension of a ½ inch by two inches by twenty six and ½ inches in height. Suitable rodless air slides comprise a one inch bore and eleven inch stroke and have associated end lugs and mount brackets, which are commercially available from McMaster-Carr. The rodless air slide is double acting and comprises a carriage that is connected to an internal piston and two compressed air ports.

The automated cleansing unit comprises two magnetic arms. The horizontal support comprising a rodless air slide is the structure upon which the two magnetic arms are mounted. The magnetic arms are mounted to the rodless air slide such that the magnetic arms move back and forth along the length of the double acting rodless air slide by the force of compressed air. Each of the magnetic arms are comprised of aluminum and have the approximate dimensions of one inch by two inches by fourteen inches in length and have a "T" shape channel that houses seven neodymium iron boron magnets (not shown). Each of the neodymium iron boron magnets has the approximate dimensions of two inches in length, one inch in width and half or an inch in height. Each of the neodymium iron boron magnets comprises a magnetic strength of 12200 Gauss, available from Edmund Scientifics. The magnetic arms are configured at a height of about 2.75 cm above the microplate holder with the caveat that the magnets maintain their function to attract and move the bodies comprised within the wells of the microplate. The magnetic arms move back and forth along the length of the rodless air slide by the force of compressed air at a speed of approximately 6 back and forth sweeps over the length of the rodless air slide over a 10 second time period.

Below the magnetic arms are configured four microplate holders. Each of the microplate holders comprise a clamping plate and four pistons attached to a pneumatic control unit. When actuated, the pistons for the pneumatic control unit hold the microplates in the four microplate holders at a pressure of from about 90 psi. Prior to placing the lidded microplates into the microplate holders of automated cleansing unit, the pneumatic control unit is turned on.

Components of the pneumatic control unit are connected to the rodless air slide, the piston and clamping plates. The pneumatic control unit is used to apply compressed air to the automated cleansing unit, which imparts a force by converting the potential energy of compressed air into kinetic energy. The pneumatic control unit comprises a solenoid air control valve, a distribution manifold outlet, a compressed air control valve, a compressed air flow regulator, an alternating output binary valve, a two-hand safety pneumatic control valve, a compressed air control valve and various connectors that provide pressurized air to the automated cleansing unit from an external air source. The air control valve, air flow regulators, alternating a binary valves, a two-hand safety pneumatic control valve are positioned upstream of a solenoid air control valve. A suitable solenoid air control valve, in one embodiment, is described as a double air style valve with a 10 psi to 120 operating pressure. Suitable compressed air flow regulators can operate in the pressure range of 14 psi to 116 psi. Suitable air control valve alternating output binary valves operate in a 35 psi to 100 psi range. All of the components of the pneumatic control unit are available from McMaster-Carr®.

The microplate holder is designed to hold four commercially available 96 well microplates. The microplate holder comprises a riser, an aluminum base plate, a clamping plate and pistons. Riser has a larger dimension than the approximately dimension of a commercially available microplate. In some embodiments, the riser has the dimensions five inches by five and ¾ inches. The riser is comprised of polyoxymethylene which is commonly known under DuPont's brand name DELRIN®® is used as a metal substitute because it is a lightweight, low-friction, and wear-resistant thermoplastic that possesses good physical and processing properties and capable of operating in temperatures in excess of 90° C. In addition to the riser, the microplate holder, in some embodiments, comprises an aluminum base plate. The aluminum base plate has a raised portion and a trench which is approximately the same dimensions as a commercially available microplate, such that the bottom of the wells rest on the raised portion and the perimeter of the microplate fit in the trench. The aluminum base plate is designed such that the microplate is not adversely affected by the compression of the clamping plate by the piston when the pneumatic pressure unit is actuated.

The aluminum base plate comprises a first heater and the clamping plate comprises a second heater. The first heater and second heater comprise flexible silicone rubber heaters available from Omega.com. The first heater and the second heater can be controlled by a ¼ DIN six zone temperature controller with RS-232 communications and free configuration software available by from Omega.com. The first heater and the second heater are used to stabilize the temperature of the sample and the skin mimic at room temperature ranging from about 20° C. to about 25° C. Prior to placing the lidded microplates into the microplate holders of automated cleansing unit, the first heater and the second heater are turned on to stabilize the temperature of the sample and the skin mimic at room temperature ranging from about 20° C. to about 25° C.

The lidded microplates are placed into the microplate holders and pneumatic control unit is actuated such that the lidded microplates are held under 90 psi of pressure. The magnetic arms are actuated on and arms moves over the lidded microplates at a height of 2.65 cm above the microplate holders. The magnetic arms of the automated cleansing unit, sweep back and forth over the microplate holders for 5 minutes, at a speed of 6 sweeps per every 10 seconds. After 5 minutes of the automated cleansing process, the lidded microplates are removed from the microplate holders and are disassembled so that spectral data is gathered by a spectrophotometer for both pieces of skin mimic surface material.

Prior to the spectral readings, two large 4000 ml beakers of 20° C. to 25° C. water are filled. The first piece of skin mimic is removed from the first microplate and submerged in the tap water within the first beaker five times. The second piece of skin mimic is removed from the second microplate and submerged within the second beaker five times. The completeness of rinsing step is judged visually by the lack of foam on the skin mimic and presence of defined circles of deposited material on the skin mimic. Both piece of skin mimic are blotted with paper towels and fumed in a drying hood for five minutes each. The reading surface of the spectrophotometer is cleaned. The first piece of skin mimic is placed on the reading surface with the textured and treated region of the first skin mimic facing the spectrophotometer. Next, a piece of plastic having a plurality of holes which correspond in size to the openings of the microplate is placed over the textured and treated region of the first skin mimic. The scan is then performed using the robot arm of the spectrophotometer. The baseline spectral data for the first piece of skin mimic material is saved for comparison with the first baseline. The reading surface of the spectrophotometer is cleaned and the spectral data for the second piece of skin mimic surface material is obtained by the aforesaid method. The baseline spectral data for the second skin mimic surface material is saved on a computer for comparison with the second baseline.

The spectrophotometer measures the L-a-b values for the skin mimic surface material before cleansing and after washing. The deposition values of the in-vitro method are reported as a Delta L value and are indicative of the deposition profile of each sample. The difference of the light intensity L or "Delta-L" is the L value after the cleansing-L value before cleansing (the baseline spectral data).

The Deposition Method is also available in U.S. Patent Application Pub. No. 20100158830.

EXAMPLES

Inventive Example 1 is a skin cleansing composition which can be included as part of an aerosol foam skin cleanser.

|  | Inventive Example 1 |
|---|---|
| Branched sodium trideceth-2-sulfate ST2S | 9.21% |
| Cocamidopropyl betaine | 2.75% |
| Trideceth-3 Iconal TDA-3-Ethoxylated Tridecyl Alcohol | 1.31% |
| Sodium Chloride | 4.02% |
| Guar, Hydroxypropyl Trimonium Chloride, N-Hance CG-17 | 0.34% |
| Acrylates/C10-30 Alkyl Acrylates Cross Polymer | 0.027% |
| PEG-90M | 0.12% |
| Xanthan gum | 0.26% |
| Petrolatum | 10% |
| Soybean Oil | 4.85% |
| Monoglyceryl Monooleate | 0.1% |
| Butylated hydroxyltoluene (BHT) | 0.098% |
| Disodium EDTA | 0.13% |
| Sodium Benzoate | 0.27% |
| Preservative | 0.033% |
| Perfume | 0.25% |
| Water | Q.S |
| pH (using, citric acid to adjust) | 5.7 |

Inventive Example 1 is a blended multiphase composition, wherein the benefit phase (including petrolatum, soybean oil, butylated hydroxyltoluene, and monoglyceryl monooleate) is dispersed in a cleansing phase. This composition is made by adding water to a main mixing vessel. Sodium chloride, xanthan gum, guar hydroxypropyltrimonium chloride, and sodium trideceth sulfate are added to the water with constant mixing. While that is mixing, a polymer premix is prepared by combining Acrylates/C10-30 Alkyl Acrylates and PEG-90M into trideceth-3 with mixing. Once the polymer premix is dispersed, the premix is added to the main mixing vessel. Cocamidopropyl betaine, EDTA, and sodium benzoate are then sequentially added to the main mixing vessel with mixing. The pH is then adjusted to about 5.7 with the addition of a pH modifier (like citric acid). Preservative and perfume are then added with mixing.

The benefit phase is prepared by first creating a lipid premix by heating soybean oil to about 50° C. in a separate vessel. Monoglyceryl monooleate and butylated hydroxyltoluene are added to the soybean oil with mixing. The lipid premix is then added to the main vessel with stirring. In a separate vessel, petrolatum is heated to about 88° C. with mixing. The petrolatum is then cooled to about 60° C. and added to the main mixing vessel with mixing. The composition is mixed until homogenous.

Inventive Examples 2-7 are of aerosol foam skin cleansers including a skin cleansing composition (Inventive Example 1), a low pressure foaming agent, and a package.

|  | Inventive Example 2 | Inventive Example 3 | Inventive Example 4 | Inventive Example 5 | Inventive Example 6 | Inventive Example 7 |
|---|---|---|---|---|---|---|
| Inventive Example 1 | 97% | 95% | 92% | 97% | 95% | 92% |
| Foaming agent (25 wt % isobutane & 75 wt % isopentane) | 3% | 5% | 8% | — | — | — |
| Foaming agent (n-butane) | — | — | — | 3% | 5% | 8% |
| Packaging | Bag On valve | Bag On valve | Bag On valve | Bag On valve | Bag On valve | Bag On valve |
| Propellant - compressed air filled to 12-15 psi | Yes | Yes | Yes | Yes | Yes | Yes |
| Foam Density (g/ml) | 0.4 | 0.26 | 0.15 | 0.27 | 0.10 | 0.06 |
| Foam Rheology - Young's Modulus (Pa) | 61 | 32 | 6 | 15 | 10 | 7.6 |
| Foam Rheology Zero Sheer Viscosity (Pa · S) | 1571 | 694 | 201 | 444 | 325 | 298 |
| Petrolatum Deposition ($\mu g/cm^2$) | 803 | 430 | 532 | 558 | 363 | 284 |
| Soy bean oil Deposition ($\mu g/cm^2$) | 60 | 49 | 60 | 47 | 38 | 49 |

Inventive Examples 2-7 are made by first premixing the skin cleansing composition with foaming agent in a closed system and then injecting the mixture into a bag which is fastened to a valve through the standard crimping process. Then, the valve with bag and mixture is crimped onto a can (either metal, plastic, or glass). Then, propellant is added into the can, but outside of the bag to provide a positive pressure differential outside of the bag.

Inventive Example 8 is a skin cleansing composition which can be included as part of an aerosol foam skin cleanser.

|  | Inventive Example 8 |
|---|---|
| Branched sodium trideceth-2-sulfate ST2S | 23% |
| Cocamidopropyl betaine | 7% |
| Trideceth-3 Iconal TDA-3-Ethoxylated Tridecyl Alcohol | 1.86% |
| Sodium Chloride | 4.75% |
| Guar, Hydroxypropyl Trimonium Chloride, N-Hance CG-17 | 0.4% |
| Soybean Oil | 4.85% |
| Monoglyceryl Monooleate | 0.05% |
| Butylated hydroxyltoluene (BHT) | 0.098% |
| Disodium EDTA | 0.13% |
| Sodium Benzoate | 0.27% |
| Preservative | 0.033% |
| Perfume | 0.25% |
| Water | Q.S |
| pH (using citric acid to adjust) | 5.7 |

Inventive Example 8 is a blended multiphase composition, wherein the benefit phase (including soybean oil, butylated hydroxyltoluene, and monoglyceryl monooleate) is dispersed in the cleansing phase. This composition is made by adding water to a main mixing vessel. Sodium chloride, guar hydroxypropyltrimonium chloride, sodium trideceth sulfate, and cocamidopropyl betaine are added to the water with constant mixing. Then add EDTA and sodium benzoate. The pH is then adjusted to about 5.7 with the addition of a pH modifier (like citric acid). Then add the preservative and perfume with good mixing.

The benefit phase is prepared by first creating a lipid premix by heating soybean oil to about 50° C. in a separate vessel. Monoglyceryl monooleate and butylated hydroxyltoluene are added to the soybean oil with mixing. The lipid premix is then added to the main vessel with stirring. The composition is mixed until homogenous.

Inventive Example 9 is an aerosol foam skin cleanser including a skin cleansing composition (Inventive Example 8), a low pressure foaming agent, and a package.

|  | Inventive Example 9 |
|---|---|
| Skin Cleansing Composition (Example 8) | 97.15% |
| Foaming agent (about 25 wt % isobutane & about 75 wt % isopentane) | 2.85% |
| Packaging | Bag on Valve |
| Propellant-Compressed Air filled to a pressure of about 12-15 psi | Yes |
| Foam Density (g/ml) | 0.85 |

Inventive Example 9 is made by first premixing the structured surfactant composition with foaming agent in a closed system and then injecting the mixture into a bag which is fastened to a valve through the standard crimping process. Then, the valve with bag and mixture is crimped onto a can (either metal, plastic, or glass). Then, propellant is added into the can, but outside of the bag to provide a positive pressure differential outside of the bag.

Inventive Example 10 is a skin cleansing composition which can be included as part of an aerosol foam skin cleanser.

|  | Inventive Example 10 |
|---|---|
| Branched sodium trideceth-2-sulfate ST2S | 7.8% |
| Cocamidopropyl betaine | 2.3% |
| Trideceth-3 Iconal TDA-3-Ethoxylated Tridecyl Alcohol | 1.1% |
| Sodium Chloride | 4.02% |
| Guar, Hydroxypropyl Trimonium Chloride, N-Hance CG-17 | 0.29% |

|  | Inventive Example 10 |
| --- | --- |
| Acrylates/C10-30 Alkyl Acrylates Cross Polymer | 0.023% |
| Xanthan gum | 0.22% |
| Soybean Oil | 4.85% |
| Glyceryl Monooleate | 0.05% |
| butylated hydroxyltoluene | 0.1% |
| Disodium EDTA | 0.13% |
| Sodium Benzoate | 0.27% |
| Preservative | 0.033% |
| Perfume | 0.25% |
| Water | Q.S |
| pH (using citric acid to adjust) | 5.7 |

Inventive Example 10 is a blended multiphase composition, wherein the benefit phase (including soybean oil, butylated hydroxytoluene, and monoglyceryl monooleate) is dispersed in a cleansing phase. This composition is made by adding water to a main mixing vessel. Sodium chloride, xanthan gum, guar hydroxypropyltrimonium chloride, and sodium trideceth sulfate are added to the water with constant mixing. While that is mixing, a polymer premix is prepared by combining Acrylates/C10-30 Alkyl Acrylates into trideceth-3 with mixing. Once the polymer premix is dispersed, the premix is added to the main mixing vessel. Cocamidopropyl betaine, EDTA, and sodium benzoate are then sequentially added to the main mixing vessel with mixing. The pH is then adjusted to about 5.7 with the addition of a pH modifier (like citric acid). The preservative and perfume are then added with good mixing.

The benefit phase is prepared by first creating a lipid premix by heating soybean oil to about 50° C. in a separate vessel. Monoglyceryl monooleate and butylated hydroxyltoluene are added to the soybean oil with mixing. The lipid premix is then added to the main vessel with stirring. The composition is mixed until homogenous.

Inventive Example 11 is an aerosol foam skin cleanser including a skin cleansing composition (Inventive Example 10), a low pressure foaming agent, and a package.

|  | Example 11 |
| --- | --- |
| Skin Cleansing Composition (Example 10) | 95% |
| Foaming agent (n-butane) | 5% |
| Packaging | Dip Tube |

Inventive Example 11 is made by first premixing the skin cleansing composition with foaming agent in a closed system and then injecting the mixture into a canister.

Combinations

A. A packaged aerosol foaming skin cleanser, comprising:
   i) a multiphase skin cleansing composition, comprising a structured surfactant phase and a benefit phase, wherein the structured surfactant phase comprises a branched structured surfactant, and the benefit phase comprises a hydrophobic benefit agent; wherein the multiphase cleansing composition is shear thinning and has a viscosity of about 8,000 cps to about 80,000 cps;
   ii) a low pressure foaming agent; and iii) a package.
B. The packaged aerosol foaming skin cleanser of paragraph A, wherein the low pressure foaming agent comprises n-butane, an isobutane blend, isopentane, or a combination thereof.
C. The packaged aerosol foaming skin cleanser of any paragraphs A-B, wherein the low pressure foaming agent is a combination of isobutane and isopentane with about 25 weight percent of the isobutane and about 75 weight percent of the isopentane.
D. The packaged aerosol foaming skin cleanser of any of paragraphs A-C, wherein the package is a dip tube package.
E. The packaged aerosol foaming skin cleanser of any of paragraphs A-C, wherein the package is a bag on valve package.
F. The packaged aerosol foaming skin cleanser of paragraph E, wherein the bag on valve package comprises a collapsible bag attached to a valve, wherein the multiphase skin cleansing composition is within the collapsible bag.
G. The packaged aerosol foam skin cleanser of paragraph F, wherein the bag on valve package further comprises an exterior wall at least partially surrounding the collapsible bag and a propellant between the exterior wall and the collapsible bag.
H. The packaged aerosol foam skin cleanser of paragraph G, wherein the propellant comprises n-butane, an isobutane blend, isopentane, compressed air, or a combination thereof.
I. The packaged aerosol foam skin cleanser of any of paragraphs G-H, wherein the propellant is filled to a pressure of about 12 psi to about 15 psi.
J. The packaged aerosol foaming skin cleanser of any of paragraphs A-I, wherein the multiphase skin cleansing composition is free from non-surfactant structurants.
K. The packaged aerosol foaming skin cleanser of any of paragraphs A-J, wherein the multiphase skin cleansing composition is free from humectants.
L. The packaged aerosol foaming skin cleanser of any of paragraphs A-K, wherein the skin cleansing composition comprises from about 5% to about 30%, from about 7% to about 25%, or from about 8% to about 20%, by weight of the skin cleansing composition, of the branched structured surfactant.
M. The packaged aerosol foaming skin cleanser of any of paragraphs A-L, wherein the branched structured surfactant composition comprises sodium trideceth-2 sulfate.
N. The packaged aerosol foaming skin cleanser of any of paragraphs A-M, wherein the skin cleansing composition comprises from about 3% to about 20%, or from about 5% to about 15%, by weight of the skin cleansing composition, of the hydrophobic benefit agent.
O. The packaged aerosol foaming skin cleanser of any of paragraphs A-N, wherein the hydrophobic benefit agent comprises petrolatum, soy bean oil, sucrose polyester, monoglyceryl monooleate, or a combination thereof.
P. The packaged aerosol foaming skin cleanser of any of paragraphs A-0, wherein the packaged aerosol foaming skin cleanser comprises from about 3% to about 15%, about 4% to about 12%, or about 4% to about 10%, by weight of the aerosol foaming skin cleanser, of the low pressure foaming agent.
Q. The packaged aerosol foaming skin cleanser of any of paragraphs A-P, wherein the skin cleansing composition further comprises a non-ionic low HLB emulsifier.
R. The packaged aerosol foaming skin cleanser of paragraph Q, wherein the low HLB emulsifier comprises glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, or mixtures thereof.
S. The packaged aerosol foaming skin cleanser of paragraph Q, wherein the low HLB emulsifier comprises trideceth-3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for cleansing skin and enhancing deposition of a benefit agent onto the skin comprising:
 a. providing an aerosol foamer comprising a container body, a collapsible bag contained in the container body, a low-pressure propellant disposed between the container body and the collapsible bag, the low-pressure propellant comprising air at a pressure of 20 psi or less at 21° C., and a foamable skin cleanser disposed in the collapsible bag, the foamable skin cleanser comprising:
  i. a multiphase skin cleansing composition comprising:
   1. a structured surfactant phase comprising a branched structured surfactant;
   2. a benefit phase comprising a hydrophobic benefit agent; wherein the multiphase cleansing composition is shear thinning and has a viscosity of about 8,000 cps to about 80,000 cps; and
  ii. a low pressure foaming agent;
 b. dispensing the foamable skin cleansing composition as a foam;
 c. cleansing the skin with the foam and delivering the hydrophobic benefit agent to the skin.

2. The method of claim 1, wherein the low pressure foaming agent comprises n-butane, an isobutane blend, isopentane, or a combination thereof.

3. The method of claim 1, wherein the branched structured surfactant composition comprises sodium trideceth-2 sulfate.

4. The method of claim 1, wherein the structured surfactant phase comprises a lamellar structure.

5. The method of claim 1, wherein the skin cleansing composition comprises from about 5% to about 15%, by weight of the skin cleansing composition, of the hydrophobic benefit agent.

6. The method of claim 5, wherein the hydrophobic benefit agent comprises petrolatum, soybean oil, sucrose polyester, monoglyceryl monooleate, or a combination thereof.

7. The method of claim 1, wherein the packaged aerosol foaming skin cleanser comprises from about 4% to about 10%, by weight of the packaged aerosol foaming skin cleanser, of the low pressure foaming agent.

8. The method of claim 1, wherein the skin cleansing composition comprises from about 7% to about 25%, by weight of the skin cleansing composition, of the branched structured surfactant.

9. The method of claim 1, wherein the multiphase skin cleansing composition is free from humectants.

10. The method of claim 1, wherein the multiphase skin cleansing composition is free from non-surfactant structurants.

11. The method of claim 1, wherein the cleansing phase further comprises a non-ionic low HLB emulsifier having an HLB value of about 1.5 to about 13.

12. The method of claim 11, wherein the non-ionic low HLB emulsifier comprises glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, or mixtures thereof.

13. The method of claim 12, wherein the non-ionic low HLB emulsifier comprises trideceth-3.

14. The method of claim 1, wherein the aerosol foamer is configured as bag on valve package and the collapsible bag is attached to a valve.

* * * * *